(12) United States Patent
Mandelis et al.

(10) Patent No.: US 7,045,786 B2
(45) Date of Patent: May 16, 2006

(54) METHOD OF PHOTOCARRIER RADIOMETRY OF SEMICONDUCTORS

(75) Inventors: Andreas Mandelis, 3 Scarborough Heights, Residential Primavera, Toronto (CA) M1M 2V3; Derrick Shaughnessy, Toronto (CA); Jerias Alves Batista, Sao Luis (BR); Jose A. Garcia, Toronto (CA)

(73) Assignee: Andreas Mandelis, Toronto (CA)

( * ) Notice: Subject to any disclaimer, the term of this patent is extended or adjusted under 35 U.S.C. 154(b) by 218 days.

(21) Appl. No.: 10/797,607

(22) Filed: Mar. 11, 2004

(65) Prior Publication Data

US 2004/0183019 A1   Sep. 23, 2004

Related U.S. Application Data

(60) Provisional application No. 60/454,347, filed on Mar. 14, 2003.

(51) Int. Cl.
*G01J 5/02*   (2006.01)
(52) U.S. Cl. .................................. 250/341.1
(58) Field of Classification Search ............. 250/341.1, 250/341.6; 374/142
See application file for complete search history.

(56) References Cited

U.S. PATENT DOCUMENTS 4,713,140 A * 12/1987 Tien ............................ 438/16

(Continued)

OTHER PUBLICATIONS

"Dynamics of the plasma and thermal waves in surface-modified semiconductors (invited)", Salnick et al., Rev. of Scientific Instruments, vol. 74 (1), Jan. 2003, pp. 545-549.

(Continued)

*Primary Examiner*—Otilia Gabor
(74) *Attorney, Agent, or Firm*—Lynn C. Schumacher; Hill & Schumacher

(57) ABSTRACT

The present invention relates to metrologic methodologies and instrumentation, in particular laser-frequency domain infrared photocarrier radiometry (PCR), for contamination and defect mapping and measuring electronic properties in industrial Si wafers, devices and other semiconducting materials. In particular the invention relates to the measurement of carrier recombination lifetime, $\tau$, carrier diffusivity, D, surface recombination velocities, S, carrier diffusion lengths, L, and carrier mobility, $\mu$, as well as heavy metal contamination mapping, ion implantation mapping over a wide range of dose and energy, and determination of the concentration of mobile impurities in $SiO_2$ layers on semiconductor substrates. The present invention provides a method and complete photocarrier radiometric apparatus comprising novel signal generation and analysis techniques (carrier-wave interferometry) as well as novel instrumental hardware configurations based on the physical principle of photocarrier radiometry. The method comprises (a) optical excitation of the sample with a modulated optical excitation source and (b) detection of the recombination-induced infrared emission while filtering any Planck-mediated emissions. The present invention provides an instrumental method for detecting weak inhomogeneities among semiconducting materials that are not possible to detect with conventional single-ended photocarrier radiometry. The method comprises (a) irradiating both sides of the sample with modulated optical excitation sources that are 180 degrees out of phase with respect to one another and (b) monitoring the diffusion of the interfering, separately generated carrier waves through the corresponding recombination-induced IR emissions for PCR detection, or the use of an alternative detection scheme that monitors a sample property dependent on the carrier wave transport in the sample.

70 Claims, 17 Drawing Sheets

U.S. PATENT DOCUMENTS 5,302,830 A     4/1994   Shivanandan
5,310,260 A *   5/1994   Schietinger et al. ........ 374/142
5,667,300 A     9/1997   Mandelis et al.

OTHER PUBLICATIONS

"Non-contacting measurements of photocarrier lifetimes in bulk- and polycrystalline thin-film Si photoconductive devices by photothermal radiometry", Mandelis et al., J. Appl. Phys. vol. 80 (9), Nov. 1, 1996, pp. 5332-5341.

"Relative sensitivity of photomodulated reflectance and photothermal infrared radiometry to thermal and carrier plasma waves in semiconductors", Salnick et al., J. Appl. Phys. vol. 82 (4), Aug. 15, 1997, pp. 1853-1859.

"Theoretical and experimental aspects of three-dimensional infrared photothermal radiometry of semiconductors", J. Appl. Phys. vol. 85 (10), Ikari et al., May 15, 1999, pp. 7392-7397.

"Minority carrier lifetime and iron concentration measurements on p-Si wafers by infrared photothermal radiometry and microwave phtocoductance decay", Rodriquez et al., J. Appl. Phys. vol. 87 (11), Jun. 1, 2000, pp. 8113-8121.

"Lock-in common-mode rejection demodulation: Measurement technique and applications to thermal-wave detection: Theoretical", Mandelis et al., Rev of Scientific Instruments vol. 71 (6), Jun. 2000, pp. 2440-2444.

* cited by examiner

US 7,045,786 B2

METHOD OF PHOTOCARRIER RADIOMETRY OF SEMICONDUCTORS

CROSS REFERENCE TO RELATED U.S APPLICATION

This patent application relates to, and claims the priority benefit from, U.S. Provisional Patent Application Ser. No. 60/454,347 filed on Mar. 14, 2003, which is incorporated herein by reference in its entirety.

FIELD OF INVENTION

The present invention relates to metrologic methodologies and instrumentation, in particular laser infrared photocarrier radiometry (PCR), for contamination and defect mapping and measuring electronic properties in industrial Si wafers, devices and other semiconducting materials. In particular the invention relates to the measurement of carrier recombination lifetime, $\tau$, carrier diffusivity, D, surface recombination velocities, S, and carrier diffusion lengths, L.

BACKGROUND OF INVENTION

In recent years the development of laser-induced infrared photothermal radiometry (PTR) of semiconductors in our laboratory [1–9] and elsewhere [10] as a quantitative methodology for the measurement of transport properties of semiconductors has led to several advances in the non-contact measurement of four transport parameters: bulk recombination lifetime, (two) surface recombination velocities and carrier diffusion coefficient in Si [1–10] and GaAs [11]. Reviews of the subject matter have been presented by Mandelis [12] and Christofides et al. [13]. The major advantage of PTR over other photothermal techniques, such as photomodulated thermoreflectance (PMOR), has been found to be the higher sensitivity of PTR to the photo-excited free carrier-density-wave (the modulated-laser driven oscillating electronic diffusion wave [14]) than PMOR [15,16]. This advantage exists due to domination of the free-carrier wave over the superposed thermal-wave (TW) contributions to the PTR signal. Even so, the ever-present thermal-wave contributions due to direct lattice absorption, followed by non-radiative energy conversion and black-body (thermal infrared) emissions, have resulted in PTR signal interpretational and computational difficulties due to the large number of variables involved [5].

Therefore, confidence in the measured values of the four electronic transport properties is always accompanied by the hurdle of assuring uniqueness of the measured set of parameters in any given situation. With our development of the PTR methodology as a quantitative technique for non-destructive semiconductor diagnostics, we found [4,5] that early measurements reported without regard to computational uniqueness [17] using simplified theoretical fits to frequency-scan signals cannot be unique and therefore reliable.

Several schemes to enhance the photo-excited free carrier-density-wave (or simply "carrier-wave", CW) contributions to the photothermal signal have been proposed, such as working in the high-frequency, CW-dominated, regime with PTR [12], or using a tightly focused pump laser beam in PMOR [18]. However, the presence of even a diminished TW component in high-frequency PTR has been shown [19] to have significant effects on the measured values of the transport parameters, to compromise sensitivity to the carrier wave and to complicate the task of physical interpretation of the signal, thus raising the question of uniqueness of the measured set of solid-state transport parameters.

On the other hand, very tight focusing of the pump laser beam in PMOR tends to give rise to usually undesirable non-linear thermal and electronic effects [15,20,21], besides being unable to sufficiently eliminate the TW component of the signal [22]. Therefore, given the fundamental and practical importance of developing an all-optical, non-destructive and non-intrusive diagnostic methodology for monitoring only the transport properties of semiconductors, we concluded that the search for a purely carrier-wave laser-based detection methodology must move in the direction of isolating and eliminating the superposition of thermal-wave contributions to the infrared emission spectrum. In view of the inability of photothermal semiconductor diagnostic methods [13,18] to eliminate the thermal-wave contributions, the development of infrared laser radiometry of semiconductors to optimize this task has been very promising, given the intrinsically higher sensitivity of its photothermal embodiment, PTR, to the photo-excited carrier density-wave than other photothermal techniques, notably PMOR [16].

In a photo-excited semiconductor of bandgap energy $E_G$, an externally incident optical source such as a laser beam with super-bandgap energy photons $h\nu_{vis}/E_G$ will be absorbed and can generate free carriers which may subsequently follow several deexcitation pathways as shown in FIG. 1 for an n-type material. Ultrafast decay to the respective bandedge (e.g. conduction band) through nonradiative transitions and emission of phonons, will raise the temperature of the semiconductor locally. The free carriers will further diffuse within their statistical lifetime and will recombine with carriers of the opposite sign across the bandgap or into impurity and/or defect states within the bandgap. The electron-hole recombination mechanism with or without phonon assistance will lead either to nonradiative energy conversion through phonon emissions (e.g. in indirect-gap semiconductors such as Si) which will further raise the temperature, or to radiative decay which will produce photons of near- or sub-bandgap energy. A table of radiative recombination lifetimes at 300 K in Si and other semiconductors has been compiled by Hall [23]. In the presence of impurity or defect states within the bandgap, free-carrier decay to one or more of those states may also occur through nonradiative or radiative transitions symbolized by dashed and full arrows, respectively, in FIG. 1. Again, the former will raise the temperature of the semiconductor crystal through phonon coupling to the lattice, whereas the latter will produce photons of energy $E_G-E_D \cong h\nu_{IR}$. In actual semiconductor materials, there may be a distribution of impurity and defect states into which de-excitation may occur.

Therefore, it is more relevant to consider the full spectral range of IR emissions from a photo-excited semiconductor crystal: $h\nu_{IR}=h\nu(\lambda_D)$. If the exciting super-bandgap radiation is intensity-modulated at frequency $f=\omega/2\pi$, then the photo-generated free carrier density constitutes a spatially damped carrier-density wave (CW) (or carrier-diffusion wave [14]), which oscillates diffusively away from the generating source under its concentration gradient and recombines with a phase lag dependency on a delay time equal to its statistical lifetime, $\tau$, a structure- and process-sensitive property [24]. FIG. 2 shows a virtual cross-section of a semiconductor Si wafer where an infrared emission photon distribution is produced following laser radiation absorption and carrier-wave generation. For one-dimensional geometries, such as those obtained with thin crystals and/or use of laser beams of large spotsize, only forward- and backward-emitted photons of wavelength $\lambda$ are depicted. The IR power generated at $\lambda$ within a spectral bandwidth $d\lambda$ is given by $$dP_j(z,t;\lambda) = \{W_{NR}[T_T(z,t);\lambda] + \eta_R W_{eR}(\lambda)\}_j d\lambda; j=r,t [W] \quad (1)$$

where $W_{NR}[T_T(z,t);\lambda]$ is the thermal infrared power per unit wavelength generated due to temperature rise following optical absorption, as well as due to other nonradiative decays. The subscripts (r,t) indicate back-propagating ("reflected") or forward-propagating ("transmitted") photon power. $W_{eR}(\lambda)$ is the spectral power per unit wavelength, the product of the recombination transition rate from band to band, or from bandedge to defect or impurity state, as the case may be, multiplied by the energy difference between initial and final states. $\eta_R$ is the quantum yield for IR radiative emission upon carrier recombination into one of these states. $T_T(z,t)$ is the total temperature, including background temperature, temperature increase due to thermal-wave oscillation following laser-modulated absorption and optical heating, as well as other nonradiative energy conversion pathways. Therefore, $$W_{NR}[T_T(z,t);\lambda] = W_P[T_s(z,t);\lambda] + (1-\eta_R)W_{eR}(\lambda) + W_{eH}(\lambda)$$
$$[W/\mu m] \quad (2)$$

Here, $W_P[T_s(z,t);\lambda]d\lambda$ is the familiar Planck distribution function, or spectral emissive power, representing the rate of radiative recombination within $d\lambda$, and sample volume $\Delta V = A[\alpha^{IR}(\lambda)]^{-1}$ of emitting cross-sectional area A normal to the z-axis in FIG. 2, and depth equal to the optical absorption depth at infrared wavelength $\lambda$. $\alpha_{IR}(\lambda)$ is the IR absorption coefficient at $\lambda$ and $$W_P[T_s(z,t);\lambda]d\lambda = \frac{8\pi h(c_o/n)Ad\lambda}{\lambda^5\{\exp[hc_o/\lambda nk_B T_s(z,t)]-1\}} [W] \quad (3)$$

$(c_o/n)$ is the speed of light in the medium of refractive index n. $T_s(z,t)$ is made up of only two contributions: background temperature and harmonic optical heating of the lattice at modulation frequency f. The remaining symbols in Eq. (2) have the following meanings: $W_{eH}(\lambda)$ is the thermal IR photon generation power per unit wavelength due to intra-band nonradiative de-excitation of hot carriers with energy $hv_{vis}-E_G$, FIG. 1. $(1-\eta_R)$ is the nonradiative quantum yield for recombination processes which generate total power $W_{eR}(\lambda)$ per unit wavelength.

The use of Eq. (3) in describing the thermal emissive power assumes the existence of thermal equilibrium in the semiconductor, a condition known as the Principle of Detailed Balance. It states that the rate of radiative recombination at thermal equilibrium within an emission frequency interval $dv$, centered at frequency $v$, is equal to the corresponding generation rate of electron-hole pairs by the thermal radiation field present within the semiconductor [25]. Detailed Balance is, in itself, a statement of Kirchhoff's theorem [24], according to which "for any body in (radiative) thermal equilibrium with its environment, the ratio between the spectral emissive power $W(T,\lambda)d\lambda$ and the spectral absorptivity $\alpha(T,\lambda)$, for a given photon frequency $v=c/\lambda$ and temperature T, is equal to the spectral emissive power $W_P(T,\lambda)d\lambda$, Eq. (3), of the blackbody for the same frequency and temperature".

Although a semiconductor undergoing harmonic carrier generation is not strictly in thermal equilibrium, it has been shown [19] that in low laser power interactions with electronic carriers, the semiconductor can be considered to be at electronic and thermal equilibrium during the oscillation cycle of the photo-excited carrier-wave as long as i) there exist no intense electromagnetic optical or thermal gradient fields in the semiconductor to upset the quantum configuration of the energy states, driving the structure away from electronic energy equilibrium; ii) upward electronic transitions following optical absorption result in efficient radiative de-excitations with minimal temperature increase of the lattice, or iii) even if significant temperature changes occur due to nonradiative decays which may affect the background temperature of the lattice as in the case of CW generation, however, the temperature oscillation itself amounts to only minimal thermal-wave perturbations with no significant consequence in the structure of the energetic manifold of the semiconductor.

Under these conditions electronic transitions occur essentially adiabatically, with minimum thermal energy exchange interactions across well-defined electronic state densities. It also follows that the higher the oscillation frequency, the greater the adiabatic character of the transition, leading to a stricter validation of Kirchhoff's Law through complete thermal decoupling of the CW oscillator ensemble, as experimentally observed by use of PTR [4]. Therefore, despite the large ambient radiation field oscillations, Eq. (6) is expected to remain essentially valid away from free-carrier density equilibrium in PCR. The absence of cross-coupling in the emitted power of Eq. (1) is a statement of the adiabatic superposition of thermal-infrared (Planck-mediated) emissions through the $W_{NR}[T_T(z,t);\lambda]$ term, and direct electronic infrared emissions through the $\eta_R W_{eR}(\lambda)$ term under equilibrium (i.e. constant) baseline temperature and a stationary material energy state manifold characterized by a well-defined Fermi level. A by-product of adiabaticity is that the IR spectra of thermal and recombination emissions are independent of each other, a feature which is central to the realization of PCR.

FIG. 2 shows an elementary slice of thickness dz centered at depth z in a semiconductor slab. The crystal is supported by a backing, but is not necessarily in contact with the backing. A modulated laser beam at angular frequency $\omega=2\pi f$ and wavelength $\lambda_{vis}$ impinges on the front surface of the semiconductor. The super-bandgap radiation is absorbed within a (short) distance from the surface, typically, a few $\mu m$, given by $[\alpha(\lambda_{vis})]^{-1}$ where $\alpha(\lambda_{vis})$ is the visible-range absorption coefficient of the pump radiation. The ensuing de-excitation processes generally involve radiative and nonradiative energy release components, resulting in the generation of an IR photon field in the semiconductor involving a relatively broad spectral bandwidth. At thermal and electronic equilibrium, assuming a one-dimensional geometry as a result of a large laser beam spotsize and/or thin sample, the emitted IR photons have equal probability of being directed toward the front or the back surface of the material.

A detailed account of all IR emission, absorption, and reflection processes [19] yields the expression for the total IR emissive power at the fundamental frequency across the front surface of the material in the presence of a backing support which acts both as reflector of semiconductor-generated IR radiation with spectrum centered at $\lambda$, and as emitter of backing-generated IR radiation centered at wavelength $\lambda_b$.

$$P_T \approx \int_{\lambda_2}^{\lambda_1} d\lambda [1 - R_1(\lambda)]\{1 + R_b(\lambda)[1 + \qquad (4)$$

$$R_1(\lambda)])\varepsilon_o(\lambda) \int_0^L \Delta W_P(z, \omega; \lambda) dz + [(1 + R_b(\lambda)[1 + R_1(\lambda)])W_O(T_o; \lambda) -$$

$$W_P(T_b, \lambda)e(T_b, \lambda)[1 - R_1(\lambda)]]x \int_0^L \varepsilon_{fc}(z, \omega; \lambda) dz\}$$

where $R_1$ is the front surface reflectivity, $R_b$ is the backing support material reflectivity, $\epsilon_o(\lambda)$ is the background IR emission coefficient of the material, $\epsilon_{fc}(z,\omega,\lambda)$ is the IR emission coefficient due to the free photoexcited carrier wave, $e(T_b,\lambda)$ is the spectral emissivity of the backing material, $\Delta W_p(z,\omega,\lambda)dz$ is the harmonic IR emissive power due to the harmonically varying temperature of the sample, $W_o(T_o;\lambda)$ is the unmodulated emissive spectral power per unit wavelength due to both Planck-mediated [$W_{po}(T_o,\lambda)$] and direct radiative [$\eta_R W_{eR}(\lambda)$] emissions, $W_P(T_b,\lambda)$ is the spectral emissive power per unit wavelength of the backing surface at temperature $T_b$, and [$\lambda_1,\lambda_2$] is the spectral bandwidth of the detector. Much work has been done in attempts to separate out carrier-wave and thermal-wave contributions through modulation frequency filtering [2–5], however, they are always strongly mixed and can be separated out effectively only through spectral filtering at the IR detector. The present invention is concerned with the successful separation of the carrier wave from the thermal wave and the instrumental implementation of a technique ("Photo-Carrier Radiometry") which monitors the former wave in semiconductor materials and devices exclusively.

SUMMARY OF INVENTION

The present invention consists of the development of a complete photocarrier radiometric instrumentation hardware and software metrologic system comprising novel signal generation and analysis techniques (carrier-wave interferometry) as well as novel instrumental hardware configurations based on the physical principle of photocarrier radiometry.

i) Photocarrier Radiometry

The present invention provides a non-contact, non-intrusive, and all-optical method for imaging surface and sub-surface defects, including contamination, and determining a unique set of electronic parameters of industrial Si wafers. The method comprises (a) optical excitation of the sample with a modulated optical excitation source and (b) detection of the recombination-induced infrared emission while filtering any Planck-mediated emissions.

ii) Interferometric Photocarrier Radiometry

The present invention provides an instrumental method for detecting weak inhomogeneities among semiconducting materials that are not possible to detect with conventional single-ended photocarrier radiometry. The method comprises (a) irradiating both sides of the sample with modulated optical excitation sources that are 180 degrees out of phase with respect to one another and (b) monitoring the diffusion of the interfering, separately generated carrier waves through the corresponding recombination-induced IR emissions for PCR detection, or the use of an alternative detection scheme that monitors a sample property which depends on the carrier wave transport in the sample.

The present invention provides a non destructive method for characterizing electronic properties of materials. The method comprises the steps of: irradiating at least one surface of a material with an energy beam output from a modulated or pulsed excitation source wherein a recombination-induced infrared emission is responsively emitted from the material, filtering Planck-mediated thermal emissions from the recombination-induced infrared emission to produce a filtered recombination-induced infrared emission, and detecting the filtered recombination-induced infrared emission. The method includes calculating selected electronic properties of the material by either i) fitting the detected filtered recombination-induced infrared emission to a theoretical model of the photocarrier response of the irradiated material to calculate selected properties of the material, or using suitable calibration charts or tables to extract selected electronic properties of the material by comparison of the detected filtered recombination-induced infrared emission with reference detected filtered recombination-induced infrared emissions from reference materials with known properties.

The present invention provides an apparatus for non destructive characterization of electronic properties of materials. The apparatus comprises an excitation source means for irradiating at least one surface of a material with energy beams from the optical excitation source means wherein a recombination-induced infrared emission is responsively emitted from the material, the excitation source means being a modulated or pulsed optical excitation source means. The apparatus includes a filtering means for filtering Planck-mediated emissions from the recombination-induced infrared emission to produce a filtered recombination-induced infrared emission and a detection means for detecting the filtered recombination-induced infrared emission. The apparatus includes processing means for either i) fitting the detected filtered recombination-induced infrared emission to a theoretical model of the photocarrier response of the irradiated material to calculate selected properties of the material, or ii) comparing the detected filtered recombination-induced infrared emission with reference detected filtered recombination-induced infrared emissions from reference materials with known properties.

BRIEF DESCRIPTION OF DRAWINGS

The following is a description, by way of example only, of the method and apparatus in accordance with the present invention, reference being had to the accompanying drawings, in which.

Front intact region: $\tau = 1$ ms; $D^* = 12$ cm$^2$/s, $S_1 = 10$ cm/s, $S_2 = 210$ cm/s.

Front inside the defect: $\tau = 1$ ms; $D^* = 14.9$ cm$^2$/s, $S_1 = 25$ cm/s, $S_2 = 300$ cm/s.

Back intact region: $\tau = 1$ ms; $D^* = 12$ cm$^2$/s, $S_1 = 10$ cm/s, $S_2 = 200$ cm/s.

Figure 15:
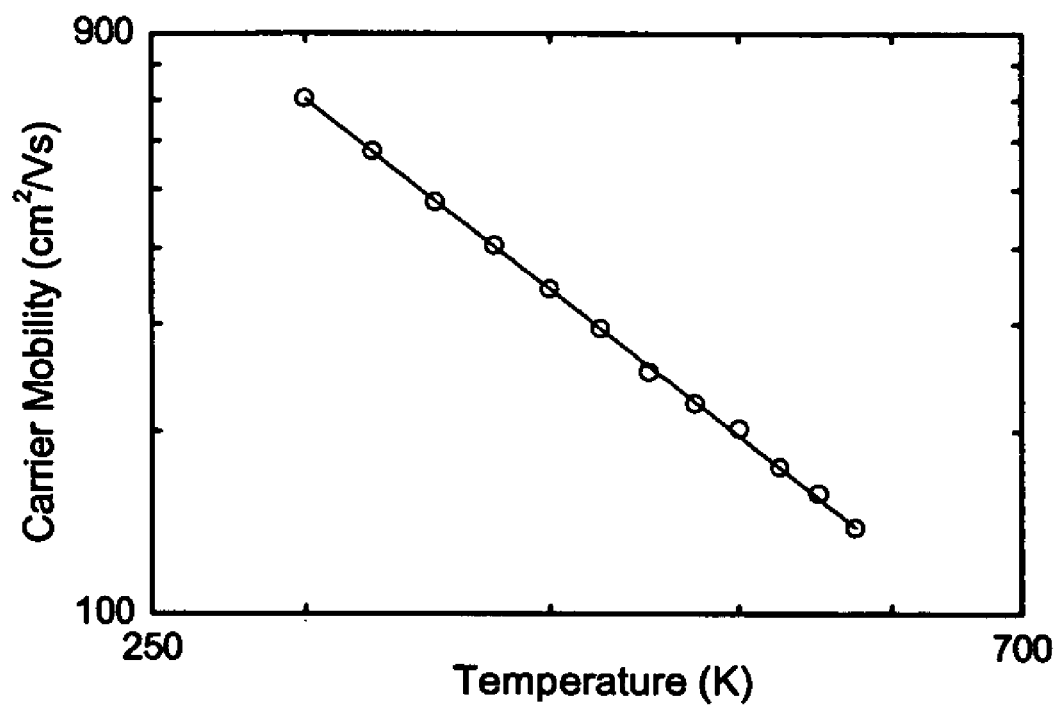

Back inside the defect: $\tau = 1$ ms; $D^* = 5$ cm$^2$/s, $S_1 = 450$ cm/s, $S_2 = 130$ cm/s FIG. 15 Temperature dependence of conductivity mobility calculated from ambipolar diffusion coefficients obtained by fitting PCR frequency scans to a theoretical model. The symbols represent experimental values while the line is the best fitting using the function $\mu(T) = \alpha \times T^b$ where $\alpha = (1.06 \pm 0.07) \times 10^9$ and $b = -2.49 \pm 0.01$.

Figure 16:
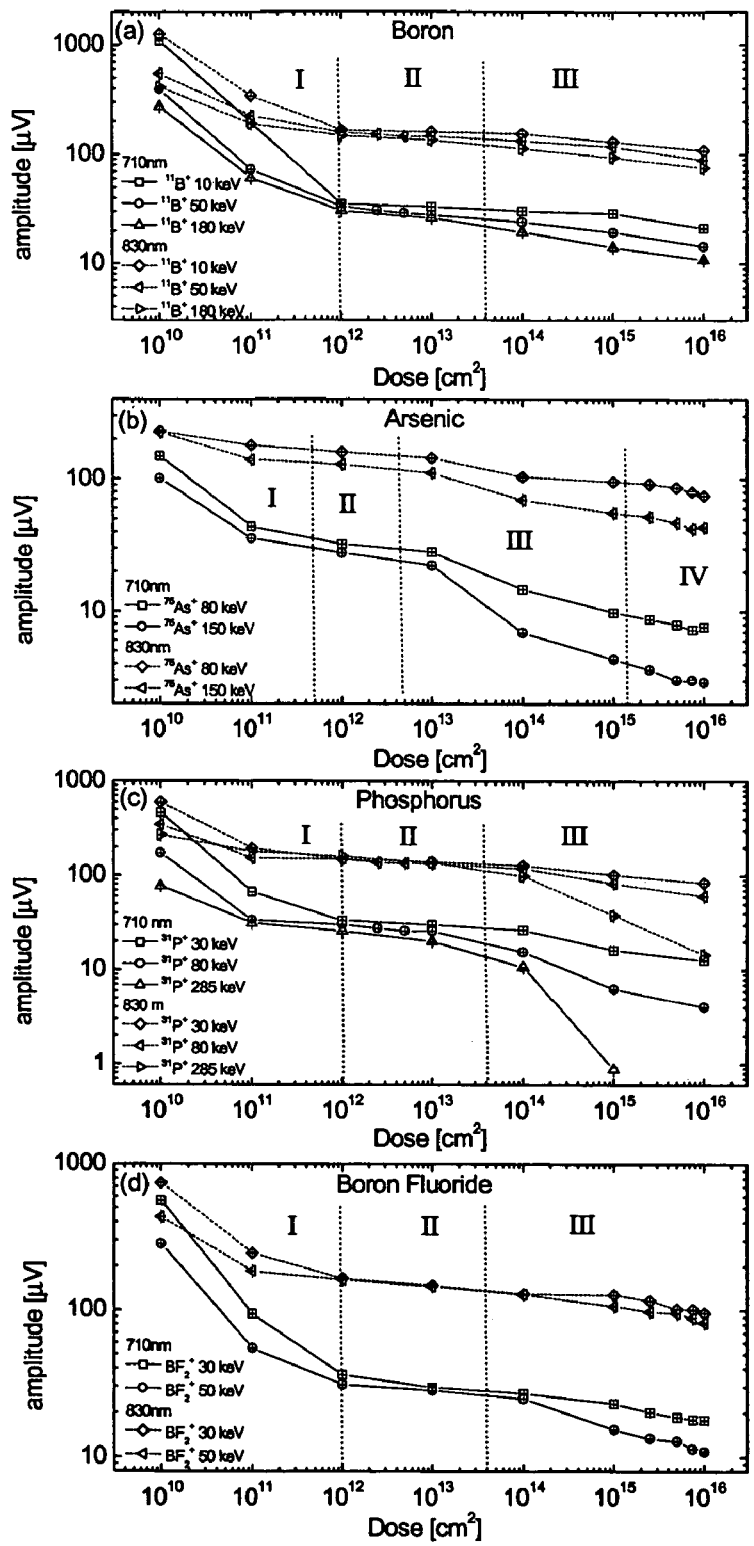

FIG. 16 PCR amplitude versus ion implant dose with 710 nm and 830 nm excitation for: (a) $^{11}B^+$, (b) $^{75}As^+$, (c) $^{31}P^+$, and (d) $BF_2^+$.

DETAILED DESCRIPTION OF THE INVENTION

A) Apparatus i) Single-Ended Photocarrier Radiometric Instrument

Figure 1:
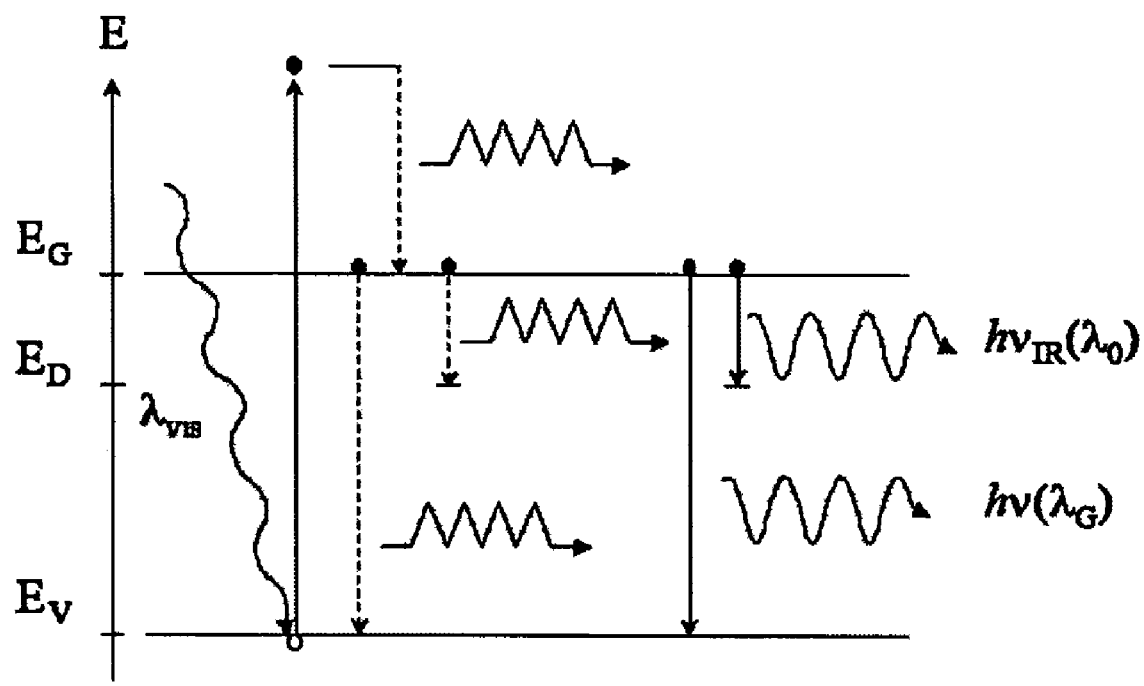
FIG. 1 shows n-type semiconductor energy-band diagram showing excitation and recombination processes. Energy emission processes include nonradiative intraband and interband decay accompanied by phonon emission, as well as direct band-to-band recombination radiative emissions of energy $h\nu(\lambda_G)$ and band-to-defect/impurity-state recombination IR emissions of energy $h\nu(\lambda_O)$.
Figure 2:
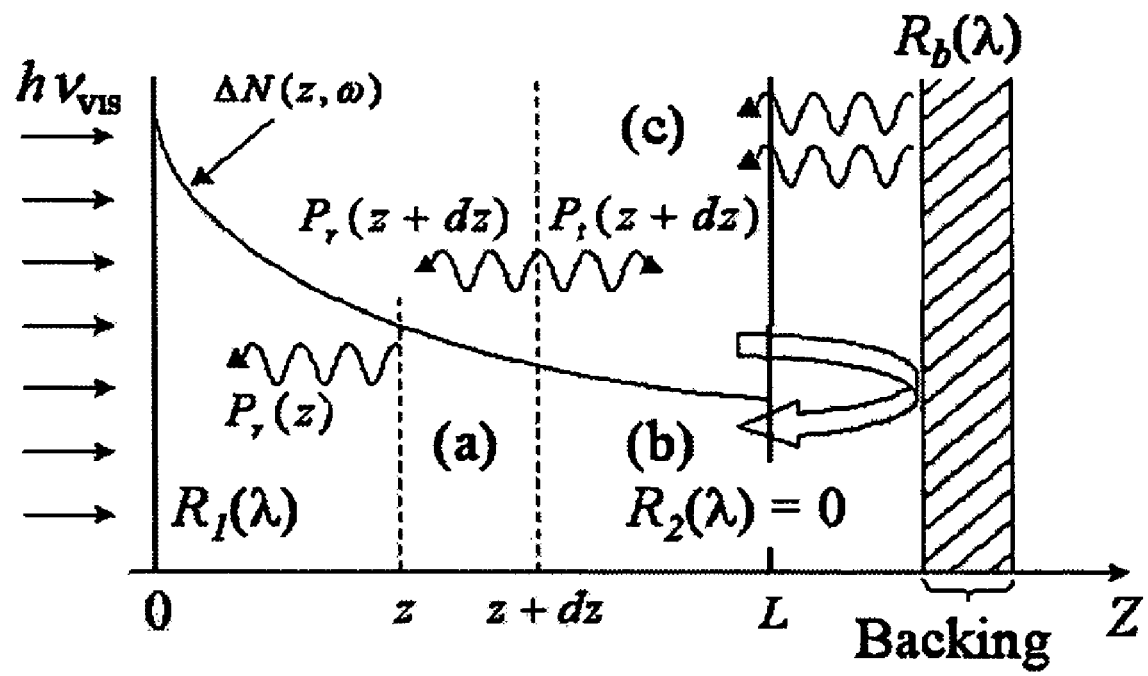
FIG. 2 shows a cross-sectional view of contributions to front-surface radiative emissions of IR photons from a) a semiconductor strip of thickness dz at depth z; b) re-entrant photons from the back surface due to reflection from a backing support material; c) emissive IR photons from the backing at thermodynamic temperature $T_b$. The carrier-wave depth profile $\Delta N(z,\omega)$ results in a depth dependent IR absorption/emission coefficient due to free-carrier absorption of the infrared photon fields, both ac and dc.
Figure 3:
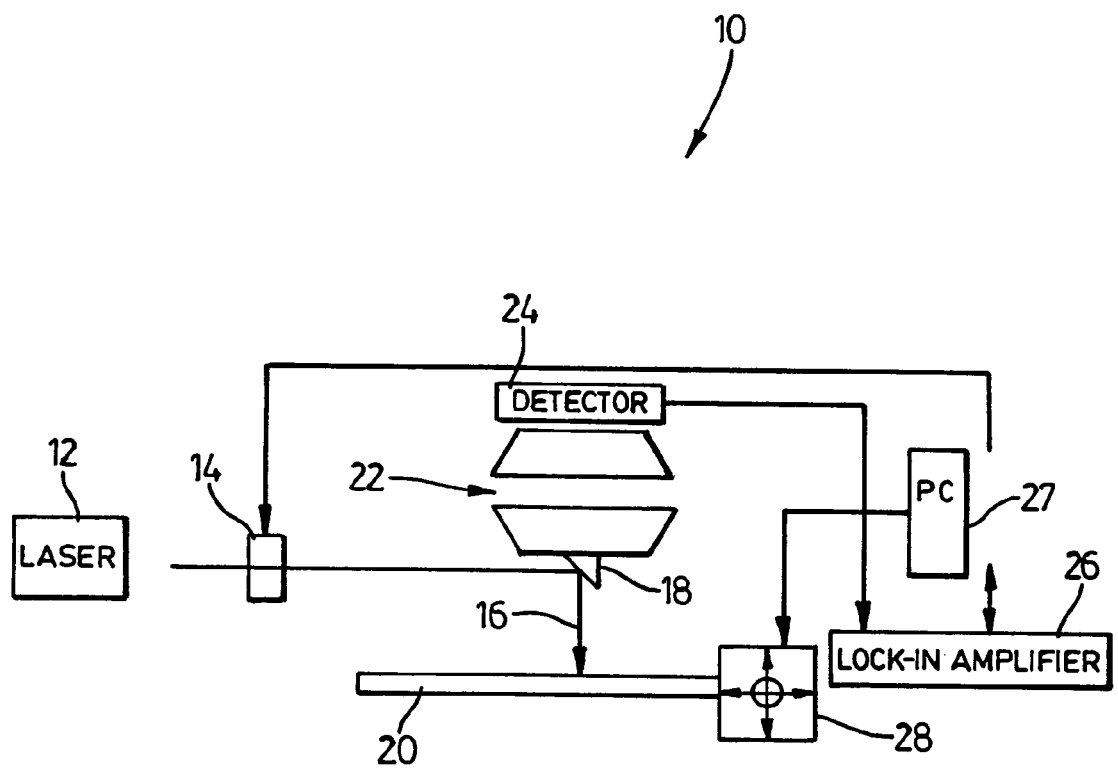
FIG. 3 shows a schematic diagram of single-ended photocarrier radiometric microscope constructed in accordance with the present invention.

A schematic diagram of a first embodiment of a novel single-ended photocarrier radiometric instrument for laser PCR for semiconductor characterization is shown at 10 in FIG. 3. The excitation source is a laser 12 capable of producing photons of energy greater than the bandgap of the sample material (hv>$E_G$). An acousto-optic modulator 14 is used to modulate the laser emissions resulting in a harmonic energy source or beam 16 that is directed using mirrors 18 and focused onto the sample 20. A pair of reflecting objectives or other suitable infrared optics, such as two off-axis paraboloidal mirrors, or one paraboloidal mirror collimator and a focusing lens 22 are aligned with the focal point coincident with that of the laser beam and used to collect emitted IR photons from the sample. The collected IR emissions are focused onto a detector 24 after being passed through a filter with a narrow spectral window that ensures the Planck-mediated thermal infrared emission band (7–12 μm) will be completely excluded from the detection range, while encompassing almost the entire emission band from the free carriers, found to be below 3 μm [26]. The signal from the detector 24 is demodulated using a lock-in amplifier 26. The entire data acquisition process is controlled using a personal computer 27, which is also connected to an XYZ motor assembly 28 to control sample positioning.

While a preferred way of filtering out the Planck-mediated thermal infrared emission band (7–12 μm) is by way of the above-mentioned filter, it will be appreciated that one could also used a detector designed to have a sufficiently low sensitivity to the Planck mediated thermal IR emissions but a high sensitivity to the PCR wavelengths.

The optical excitation source 12 in apparatus 10 may be either a pulsed or a modulated optical excitation source 32. While FIG. 3 shows the system configured with the excitation source being modulated using the AOM 14, the system may be readily modified for operation in the pulsed mode whereby the AOM 14 is removed and instead the laser 12 is operated in the pulsed mode producing a train of pulses triggered by its internal circuit or by use of external electronics with pulse duration in the sub-microsecond to sub-nanosecond range and repetition rate depending on the type of laser. When operating in pulsed mode, the signal processing is performed using one of three approaches: 1) a transient scope replaces the lockin amplifier 26 and the averaged pulse data will be stored in the scope/computer for later analysis; 2) in a hybrid mode, the lock-in amplifier 26 remains and utilizes the trigger to the pulsed laser's periodic firing of pulses as its reference and displays the fundamental Fourier component of the time-domain signal; or 3) in ultrafast applications, an optical delay line and auto-correlation signal processing are used to monitor the relaxation time of carriers.

While the apparatus 10 uses a laser as the source of optical excitation, it will be understood by those skilled in the art that any other excitation source with enough energy to excite carriers in the semiconductor or optical material under examination may be used. Detector 24 may be an imaging array sensor to rapidly image a large surface area. One could enlarge the energy beam and use the array to monitor 1-D PCR signals within each pixel, with spatial resolution determined by the imager array technology. However, one could also use the array detector with a small beam and monitor the PCR emissions as a function of position. In these area imaging applications, parallel lock-in detection schemes involving capturing the full image at least 4 times per period and performing in-phase and quadrature operations, or suitable alternative lock-in schemes, will be used.

ii) Another Configuration of Single-Ended Photocarrier Radiometric Instrument

Figure 3A:
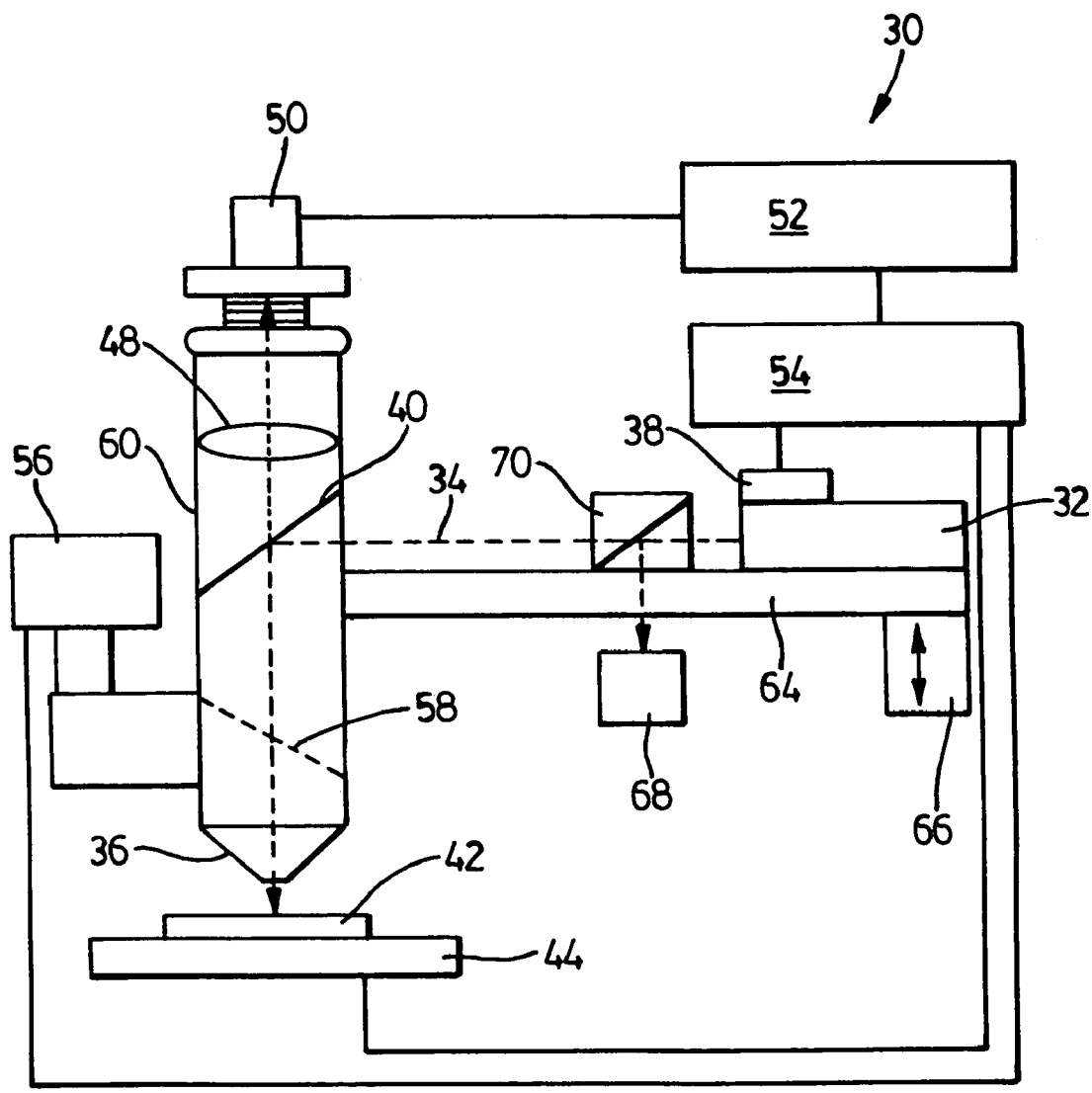
FIG. 3a shows a schematic diagram of another embodiment of a single-ended photocarrier radiometric microscope.

A schematic diagram of an alternative configuration for the single-ended photocarrier radiometric instrument used to perform the measurements on the industrial grade silicon wafers is shown generally at 30 in FIG. 3a. The excitation source is a laser 32 and is capable of producing photons of energy greater than the bandgap of the sample material ($h\nu > E_G$). The laser spot size of the exciting beam 34 is between 1-to-5 microns and controlled by using a reflective objective 36. The beam intensity at the surface of the sample is between 10-to-30 mW. A current modulator circuitry 38 is used to modulate the laser emissions resulting in a harmonic energy source that is directed using a beam splitter 40 and focused onto the sample 42. The sample 42 is mounted on a X-Y automated stage 44 for sample positioning, mapping or scanning purposes. The reflecting objective or other suitable infrared optics 36 are aligned with the focal point coincident with that of the laser beam 34 and used to collect emitted IR photons from the sample. The collected IR emissions are directed to the spectrally matched beam splitter 40 optimized for transmission within the specific spectral emission range and focused by a suitable infrared lens 48 onto a detector 50 equipped with a suitable low-noise preamplifier and a narrow spectral window so that the combination of the spectral bandwidth of detector and filter ensures the Planck-mediated thermal infrared emission band (7–12 μm) and leakage from the optical source are completely excluded from the detection range, while encompassing almost the entire emission band from the free carriers, found to be below 3 μm [26]. The signal from the detector is demodulated using a lock-in amplifier 52. As with the apparatus 10 in FIG. 3, the optical excitation source 32 in apparatus 30 may be either a pulsed or modulated optical excitation source 32.

The entire data acquisition and signal generation process is controlled using a personal computer 54, which is also connected to a CCD camera 56 and beam splitter 58 that slides in position to locate the beam spot on the sample 42. A customised microscope tube 60 is used to hold the various optics, reflective objective 36 and IR detector 50. This microscope tube and laser 32 are attached through arm 64 to the focus block 66. The photodiode 68, beam splitter 70 and focus block 66 are used to perform auto focusing by measuring the reflection of the laser beam and adjusting the sample 42 focal distance to the reflective objective 36.

iii) Interferometric Photocarrier Radiometric Instrument

Figure 4:
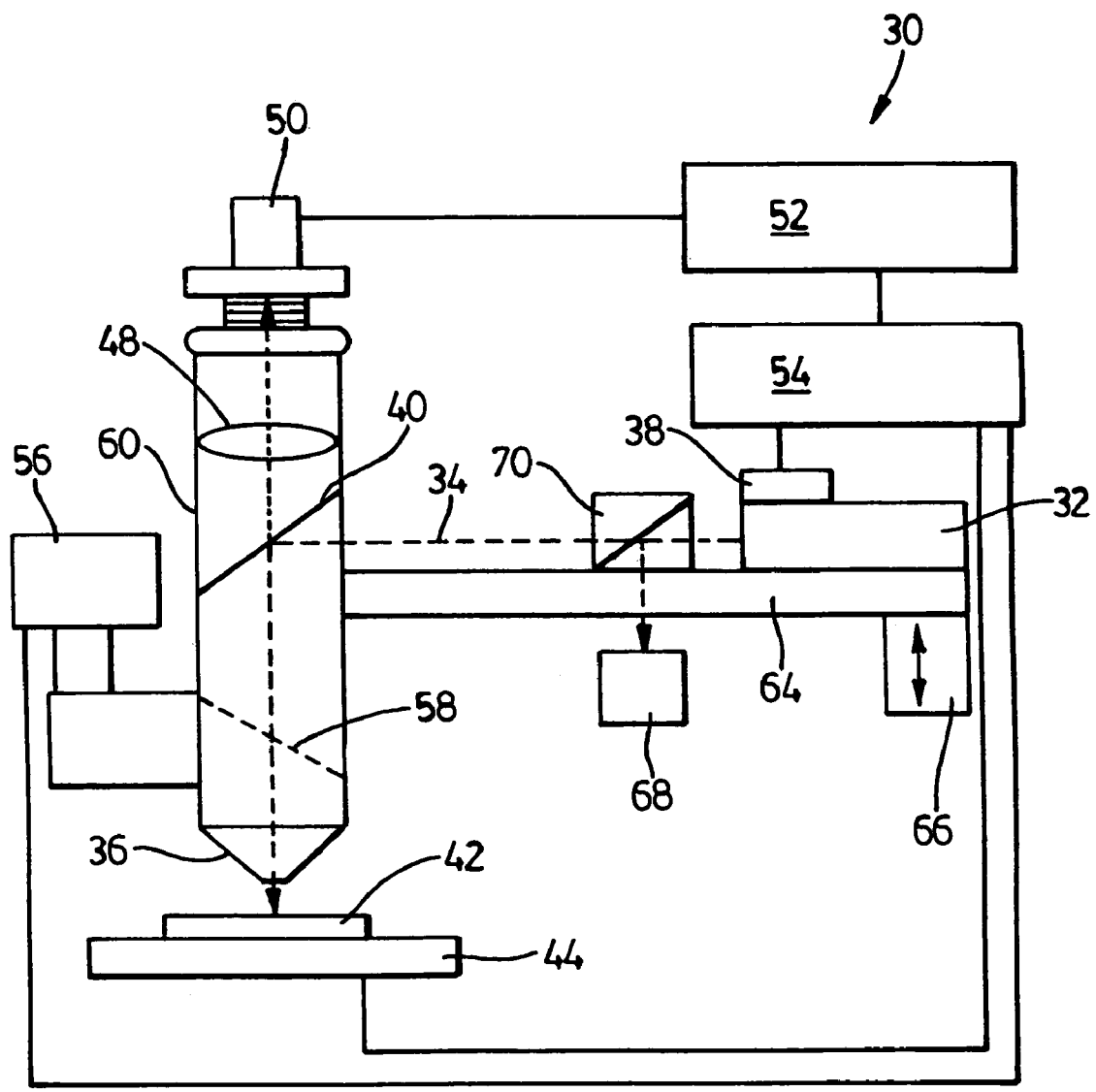
FIG. 4 shows a schematic diagram of an interferometric photocarrier radiometric microscope.

The basic components of the interferometric PCR instrument are similar to the single-ended instrument with a few significant additional components is shown generally at 80 in FIG. 4. The emissions from a single laser source 12 are split by a non-polarizing beam splitter 82. One beam 84 follows the same path as the beam in the singled ended apparatus 10 (FIG. 3) and is focused on the front surface of the sample 20. The second beam 86 is directed using a separate series of two mirrors 88, modulated using a second acousto-optic modulator 90, and focused onto the back surface of the sample 20 as beam 91. A dual function waveform generator 92 is used to produce two waveforms of identical frequency but with one phase shifted 180 degrees with respect to the other. One of the waveforms is sent to the modulator 14 for the front surface excitation beam and the other to the modulator 90 for the beam 91 directed to the back surface of the sample 20. This results in the two laser beams being modulated at identical frequencies with one having a phase lag of 180 degrees so that when one beam has maximum intensity the other has the minimum intensity and vice versa. The intensity of the beam 84 on the front surface is adjusted using a linear intensity attenuator 96 to ensure that the destructive interference of the two interfering carrier density waves results in a zero baseline PCR signal. The IR collection, data acquisition and sample positioning are identical to the single-ended PCR instrument. As with the apparatus 10 in FIG. 3, the optical excitation source 12 in apparatus 80 may be either a pulsed or modulated optical excitation source 12.

B) Methods of The Present Invention i) Photocarrier Radiometry of Electronic Materials a) Description of the Method Instrumental filtering of all thermal infrared emission contributions allows for all Planck-mediated terms to be eliminated from equation (4) yielding $$P(\omega) = \int_{\lambda_2}^{\lambda_1} d\lambda [1 - R_1(\lambda)]\{1 + R_b(\lambda)[1 + R_1(\lambda)]\}\eta_R W_{eR}(\lambda) \int_0^L \varepsilon_{fc}(z, \omega; \lambda) dz \quad (5)$$

The absorption (and, equivalently, assuming Kirchhoff's Law is valid, the emission coefficient) depends on the free-carrier density as [27]

$$\varepsilon_{fc}(z, \omega; \lambda) = \alpha_{IRfc}(z, \omega; \lambda) = \frac{q\lambda^2}{4\pi^2 \varepsilon_{oD} c^3 nm^{*2} \mu} \Delta N(z, \omega; \lambda) = C(\lambda)\Delta N(z, \omega; \alpha) \quad (6)$$

for relatively low CW densities. Here q is the elementary charge, $\epsilon_{oD}$ is the dielectric constant, c is the speed of light in the medium, n is the refractive index, m* is the effective mass of the carrier (electron or hole) and μ is the mobility. This allows the PCR signal to be expressed in the form $$P(\omega) \approx F(\lambda_1, \lambda_2) \int_0^L \Delta N(z, \omega) dz \quad (7)$$

with $$F(\lambda_1, \lambda_2) = \int_{\lambda_2}^{\lambda_1} [1 - R_1(\lambda)](1 + R_b(\lambda)[1 + R_1(\lambda)])\eta_R W_{eR}(\lambda) C(\lambda) d\lambda \quad (8)$$

The PCR signal is the integration of equation (7) over the image of the detector on the sample and thus is directly proportional to the depth integral of the carrier density in the sample. Consequently, the relative lateral concentration of any defects that affect the carrier density, either by enhancing recombination or altering diffusion coefficients, can be determined by scanning the surface of the wafer with the PCR microscope. In addition, frequency scan techniques can be used with the appropriate carrier diffusion model to obtain quantitative values for the four transport parameters [5]. This quantitative technique can be combined with the lateral maps to provide quantitative imaging of the semiconductor sample.

The optical excitation source 12 may be either a pulsed or modulated optical excitation source. Pulsed refers to a single burst of light of short duty cycle over the laser pulse repetition period, whereas modulated is essentially a repetition of square-wave pulses and a certain frequency at approx. 50% duty cycle or of a harmonic (sinewave) nature. Typically, when using a pulsed excitation source one measures response as a function of time, i.e. time domain, (essentially watching the signal decay after the short light pulse has been terminated). For modulated experiments the surface is irradiated using a repeating excitation at a given frequency (the modulation frequency) and one monitors the signal response only at this frequency, i.e. frequency domain. Pulsed responses can also be obtained using a lock-in amplifier referenced to the pulse repetition period, which monitors the fundamental Fourier coefficient of the sample response.

When using a pulsed, rather than a modulated, excitation source the PCR signal is obtained by integrating the inverse temporal Fourier transform of equation 7 over the surface area (image) of the detector [14]. Quantitative information obtained from observation of the time response of the PCR signal can then be combined with lateral maps to provide quantitative imaging of the semiconductor sample at discrete time intervals after the cessation of the laser pulse.

b) Application to Imaging of Electronic Defects in Si Wafers

I. Instrumentation and Signal Characteristics

The experimental implementation of laser infrared photocarrier radiometry is similar to the typical PTR set-up for semiconductors [4–9], with the crucial difference being that the spectral window of the IR detector and/or optical filter, and the modulation frequency response of the preamplifier stage, must be tailored through spectral bandwidth matching to a combination of carrier recombination emissions and effective filtering of the Planck-mediated thermal infrared emission band and of the synchronously modulated optical source. Conventional PTR utilizes photoconductive liquid-nitrogen-cooled HgCdTe (MCT) detectors with spectral bandwidth in the 2–12 μm range. This includes the thermal infrared range, 7–12 μm, and only part of the electronic emission spectrum at shorter wavelengths. Unfortunately, the spectral detectivity responses of MCT detectors are heavily weighed toward the thermal-infrared end of the spectrum [28]. In addition, the physics of PTR signal generation involves a substantial contribution from the thermal-wave component resulting from direct absorption by the lattice and by non-radiative recombinations of photo-excited carriers [16]. The result is an infrared signal with unequal superposition of recombination and thermal emission responses with a larger weight of the thermal infrared component.

From preliminary studies with several IR detectors and bandpass optical filters it has been observed that emissive infrared radiation from electronic CW recombination in Si is centered mainly in the spectral region below 3 μm [26]. Among those, InGaAs detectors with integrated amplifiers, a visible radiation filter and a spectral response in the <1800-nm range, was found to be most suitable, exhibiting 100% efficient filtering of the thermal infrared emission spectrum from Si as well as maximum signal-to-noise ratio over InGaAs detectors with separate amplifiers and InAs detectors. Therefore, infrared PCR was introduced using an optimally spectrally matched room-temperature InGaAs photodetector (Thorlabs Model PDA255) for our measurements, with a built-in amplifier and frequency response up to 50 MHz. The active element area was 0.6 mm$^2$ with a spectral window in the 600–1800 nm range with peak responsivity 0.95 A/W at 1650 nm. The incident Ar-ion laser beam size was 1.06 mm and the power was 20–24 mW. The detector was proven extremely effective in cutting off all thermal infrared radiation: Preliminary measurements using non-electronic materials (metals, thin foils and rubber) showed no responses whatsoever. Comparison with conventional PTR results was made by replacing the InGaAs detector with a Judson Technologies liquid-nitrogen-cooled Model J15D12 MCT detector covering the 2–12 μm range with peak detectivity $5 \times 10^{10}$ cmHz$^{1/2}$W$^{-1}$.

Figure 5:
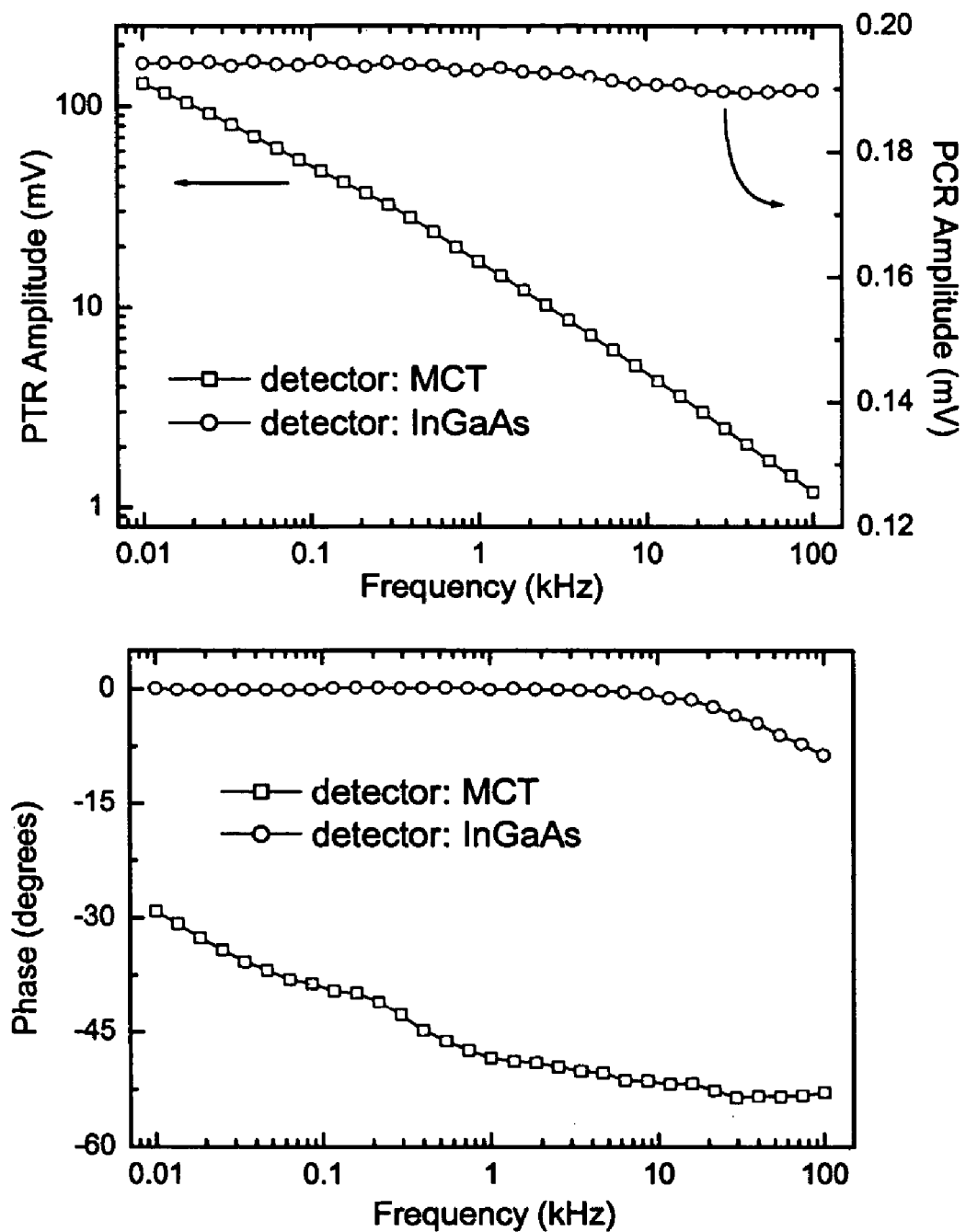
FIG. 5 Comparison of normalized PTR (MCT detector) and PCR (InGaAs detector) signals from an AlGaAs quantum well array on a GaAs wafer. Incident laser power: 25 mW.
Figure 6:
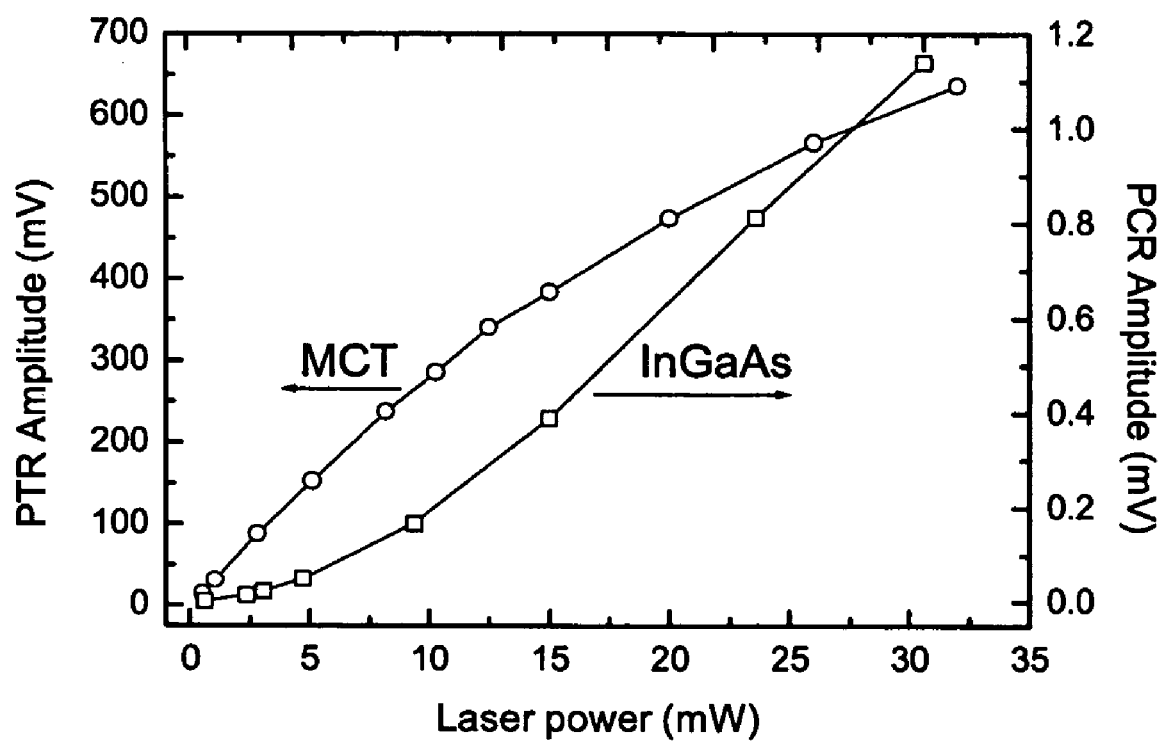
FIG. 6 PCR and PTR signal dependencies on the power of the excitation Ar-ion laser. The sample was a p-type Si wafer of resistivity $\rho \sim 20$ ςcm. Both phases were essentially constant within the 0–35 mW range.

FIG. 5 shows two frequency responses from a test AlGaAs quantum well array on GaAs substrate using both the MCT and the InGaAs detectors. The MCT response is characteristic of thermal-wave domination of the PTR signal throughout the entire modulation frequency range of the lock-in amplifier. On the other hand, the PCR signal from the InGaAs detector/preamplifier exhibits very flat amplitude, characteristic of purely carrier-wave response and zero phase lag up to 10 kHz, as expected from the oscillation of free carriers in-phase with the optical flux which excites them (modulated pump laser). The apparent high-frequency phase lag is associated with electronic processes in the sample. The PTR signals were normalized for the instrumental transfer function with the thermal-wave response from a Zr alloy reference, whereas the PCR signals were normalized with the response of the InGaAs detector to a small fraction of the exciting modulated laser source radiation at 514 nm. Regarding the well-known non-linearity of PTR signals with pump laser power [29], FIG. 6 shows a non-linear response from the PTR system at laser powers >5 mW. The PCR system, however, exhibits a fairly linear behavior for powers >15 mW and up to 35 mW, within the range of the present experiments. The non-linear behavior below 15 mW is due to surface state annihilation associated with the semiconductor sample used for these measurements.

Figure 7:
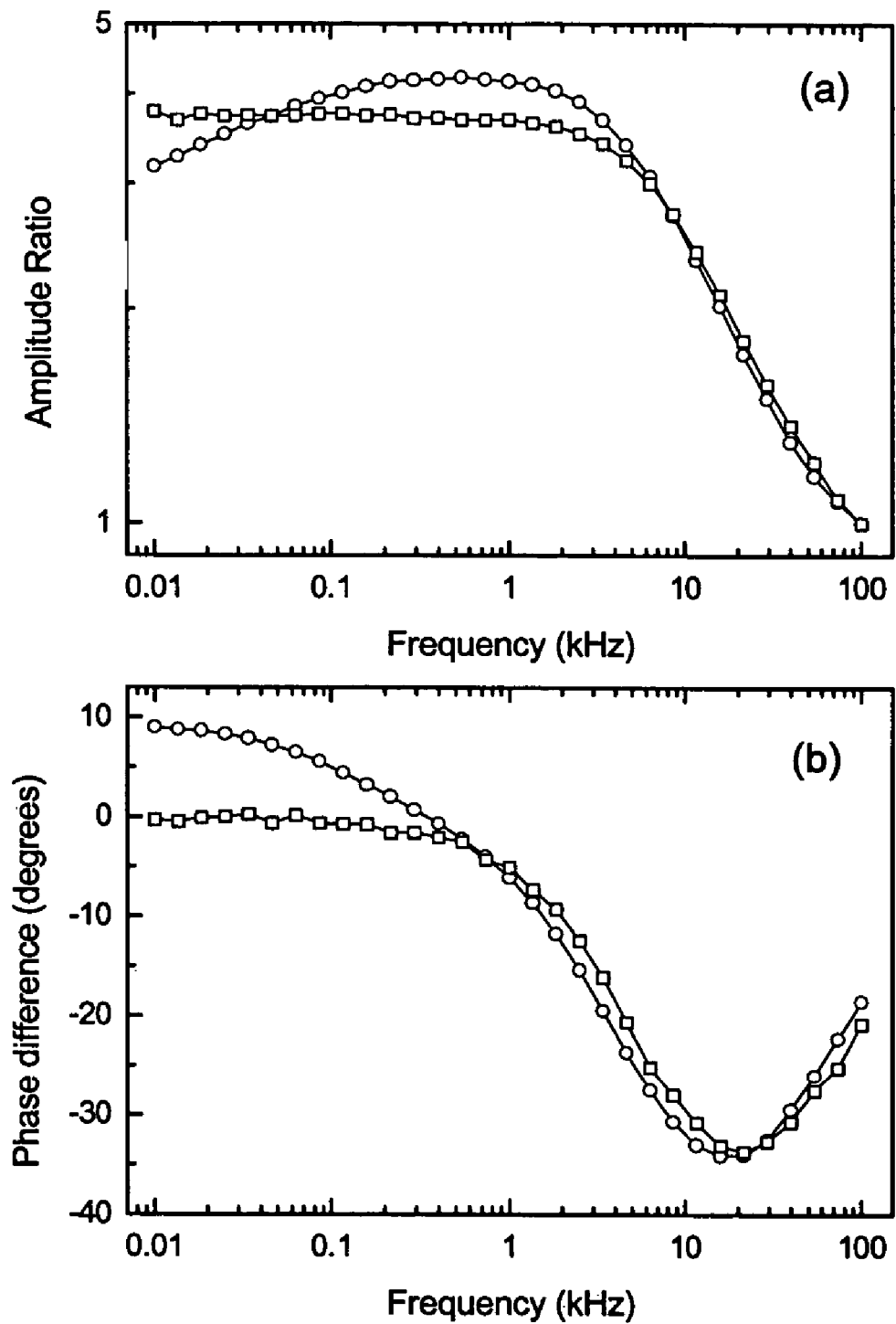
FIG. 7 (a) Self-normalized PCR and PTR signal amplitudes and (b) phases from two locations on an inhomogeneous n-type Si wafer using 20-mW Ar-ion laser and 1.2-mm beam size. $\forall$: PCR technique; –: PTR technique.

Unlike the readily available thermal infrared emissions from well-controlled reference samples for the purpose of instrumental signal normalization in semiconductor PTR [30], the quest for suitable reference samples for PCR is a much more difficult problem because of the absence of detector response in the thermal infrared spectral region. An indirect normalization method was introduced as shown in FIG. 7. Furthermore, a normalization procedure using a small fraction of the excitation laser beam may also be suitable, as the InGaAs detector is extremely sensitive to light intensity and its wavelength and some scattered optical source light may be allowed to leak into the detector and its intensity modulation frequency scanned to obtain the system transfer function. Therefore, frequency scans on a Si wafer with a large degree of signal variation across its surface were obtained from two such locations with very different responses, using both the MCT and the InGaAs detectors. Then the amplitude ratios and phase differences between the two locations using the same detector were plotted and the amplitude ratios were further normalized at 100 kHz, FIG. 7a. These self-normalized data are independent of the instrumental transfer function and depend only on differences among electronic parameters (PCR) or combinations of thermal and electronic parameters (PTR) at the two coordinate locations.

Upon superposition of the self-normalized signals it was found that both amplitude and phase curves essentially overlapped within the electronic region. This implies that both detectors monitor the same electronic CW phenomena at high frequencies and thus the instrumental normalization of the PCR signal can be performed by 1) using the PTR signal from a high-electronic-quality reference Si wafer, normalized by a simple one-dimensional thermal-wave frequency scan of a homogeneous metallic solid [5]; 2) mathematically extracting the electronic component of the PTR signal [5] and adjusting the PCR signal to this component; and 3) using the PCR amplitude and phase frequency correction functions for all other signal normalizations. This indirect scheme was proven satisfactory. It will be seen in part b) of this section, however, that the small differences in the self-normalized high-frequency signals of FIG. 7 are indicative that the thermal-wave component of the PTR signal can be present even at the highest modulation frequencies and, without independent knowledge of the electronic properties of the reference semiconductor, it can affect their "true" values significantly, a conclusion we also reached about photomodulated thermoreflectance [22]. Normalizing the PCR signals with a small scattered portion of the incident optical source remains by far the easiest and most straightforward method, provided other instrumental complications do not arise.

II. Effects of Backing Material

Figure 8:
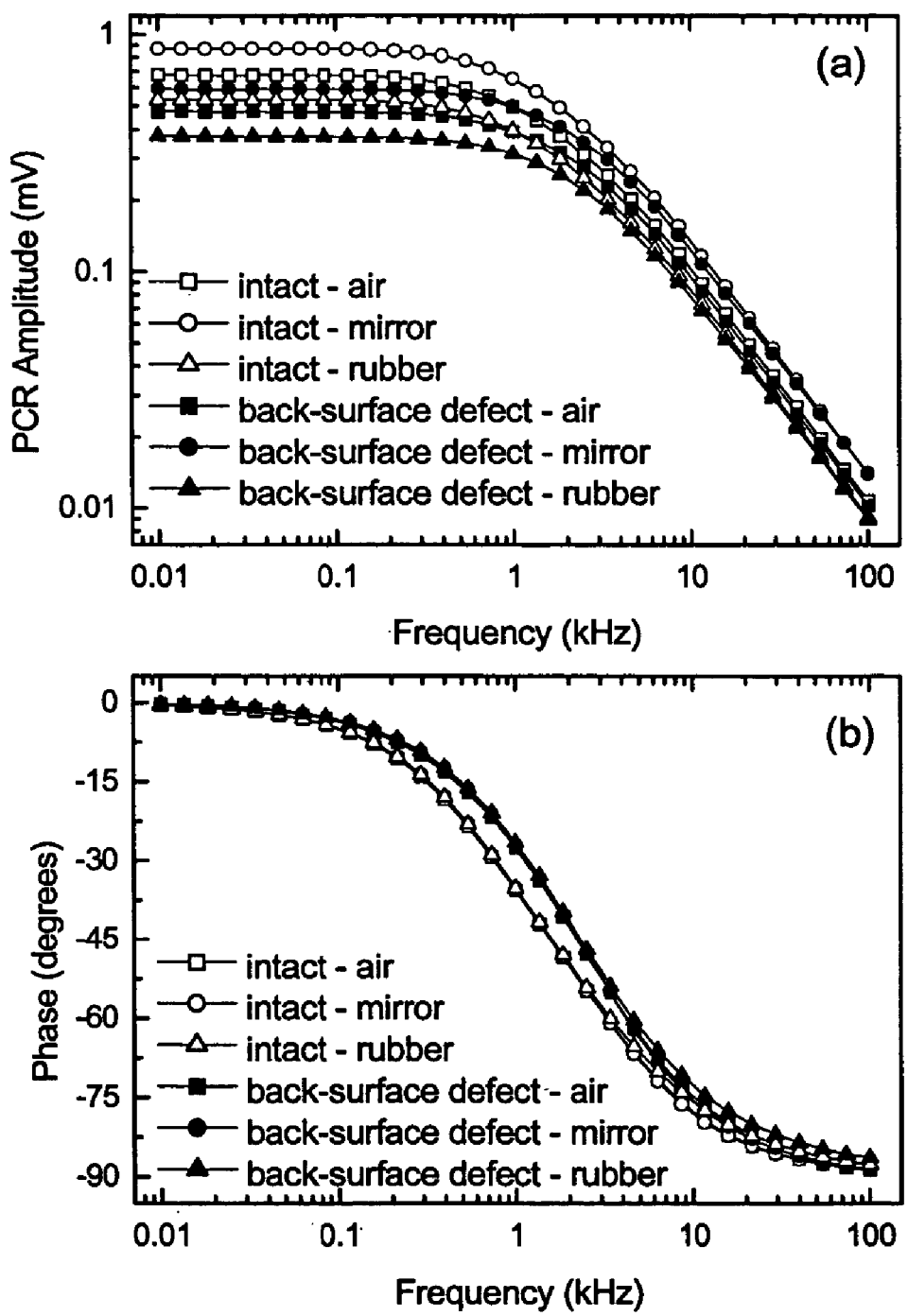
FIG. 8 PCR frequency scans from the p-type Si wafer of FIG. 6 with air and two backing supports. Laser-beam power 25 mW. (a) Amplitudes, and (b) phases.

A small area of the back surface of the Si wafer which was used for the signal linearity studies was very slightly damaged through gentle rubbing with sandpaper. PCR frequency scans were obtained from outside and inside the region with the back-surface defect. Then line scans and 2-dimensional images at fixed frequency were obtained covering the defect area. The wafer was suspended in air using a hollow sample holder, or was supported by a black rubber or by a mirror backing. FIG. 8 shows PCR frequency scans for all three backings. The PCR technique resolves the amplitudes from the three backings in the order $S_M > S_A > S_R$, (M: mirror, A: air, R: rubber).

Figure 9:
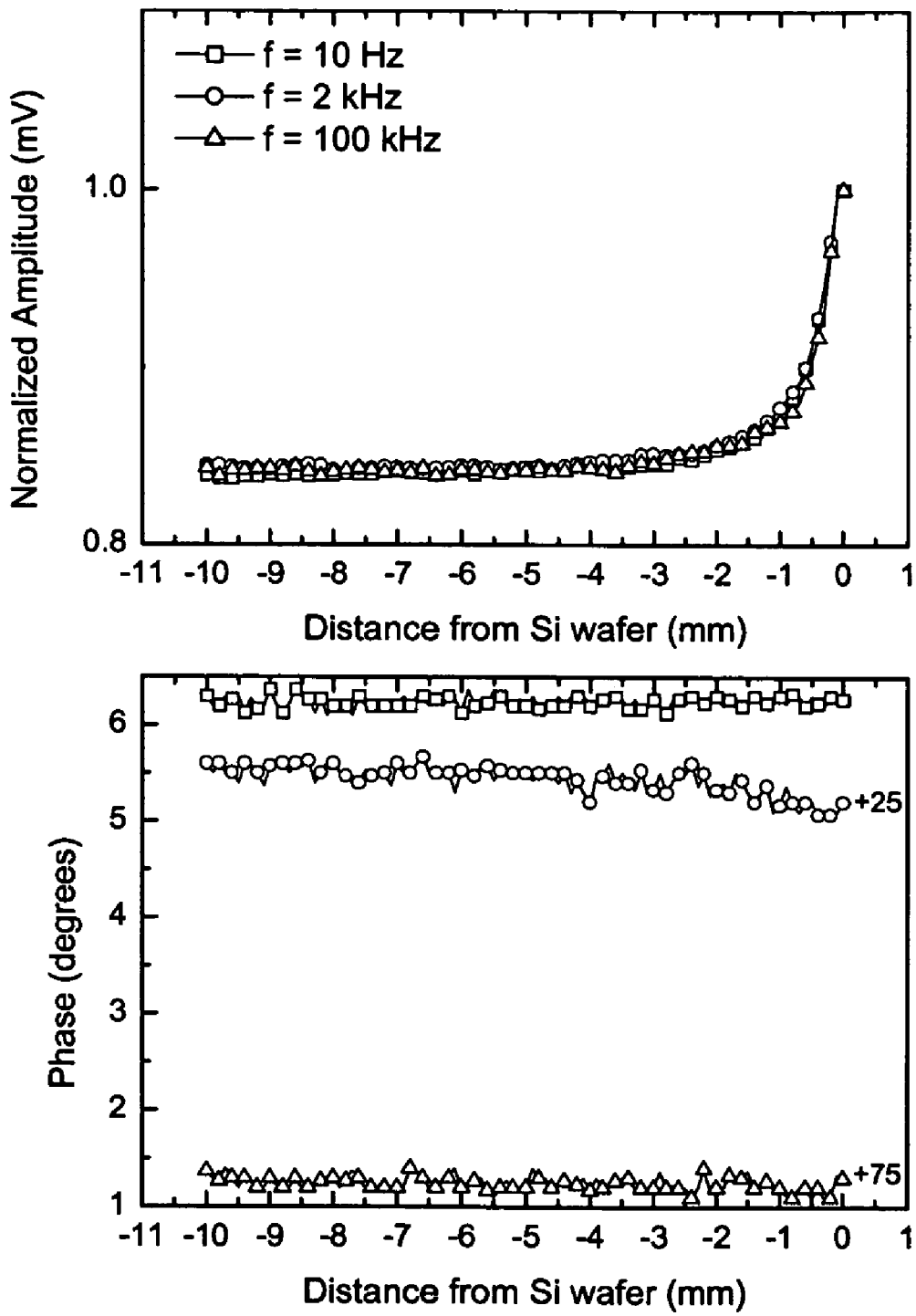
FIG. 9 PCR distance scans between an intact back-surface region of the Si wafer and a highly reflective aluminum foil-covered substrate. All amplitude curves have been normalized to unity at the wafer back-surface; phase curves indicate the offset (in degrees) of the experimental phase for convenience. Laser power: 24 mW.

To understand the origins of the signal changes in the presence of a backing support, a highly reflecting aluminum-foil-covered backing was placed at a variable distance from the back-surface of the Si wafer across from an intact region and PCR signals were monitored, FIG. 9. It is observed that the PCR amplitude remains constant for all three frequencies up to a distance of ~1 mm away from contacting the back surface, where it starts to increase. The curves are normalized to their value on the surface to show that the rate of increase is independent of frequency. The PCR phase remains essentially flat throughout.

To determine the origin of PCR signal variations with backing (whether due to IR photon internal reflections or backing emissivity changes [31]) the laser was turned off and a mechanical chopper was placed at some distance away from the IR detector. The lockin amplifier signals from the InGaAs detector nearly vanished at ~5 μV, a baseline value that remained constant for all combinations of wafer, chopper, and the three substrate materials. These dc emissivity experiments with the InGaAs detector in place are clear evidence that its spectral bandwidth lies entirely outside the thermal IR (Planck) emission range of the Si wafer with or without substrate. Therefore, the PCR amplitude enhancement for mirrored and rubber backings, FIG. 8a, is consistent with simple reflection of exiting (transmitted) CW-generated IR photons at the surface of the backing, with no possibility for thermal infrared emissivity contributions from the backing itself. The order of the PCR amplitude curves indicates that the surface of highest reflectivity (mirror) yields the strongest signal. It appears the Si-air interface is a more efficient back-scatterer of IR photons than the Si-black rubber interface, where these photons are expected to be more readily absorbed by the rubber. From Eq. (5) it is expected that the ratio of PCR signals with mirror and black rubber backings should be approximately $[2+R_1(\lambda)]/[1+R_b(\lambda)][1+R_1(\lambda)]] \approx 1.94$. The measured ratio from the low-frequency end in FIG. 8a is 1.8.

III. PCR Imaging of Deep Sub-Surface Electronic Defects

Figure 10:
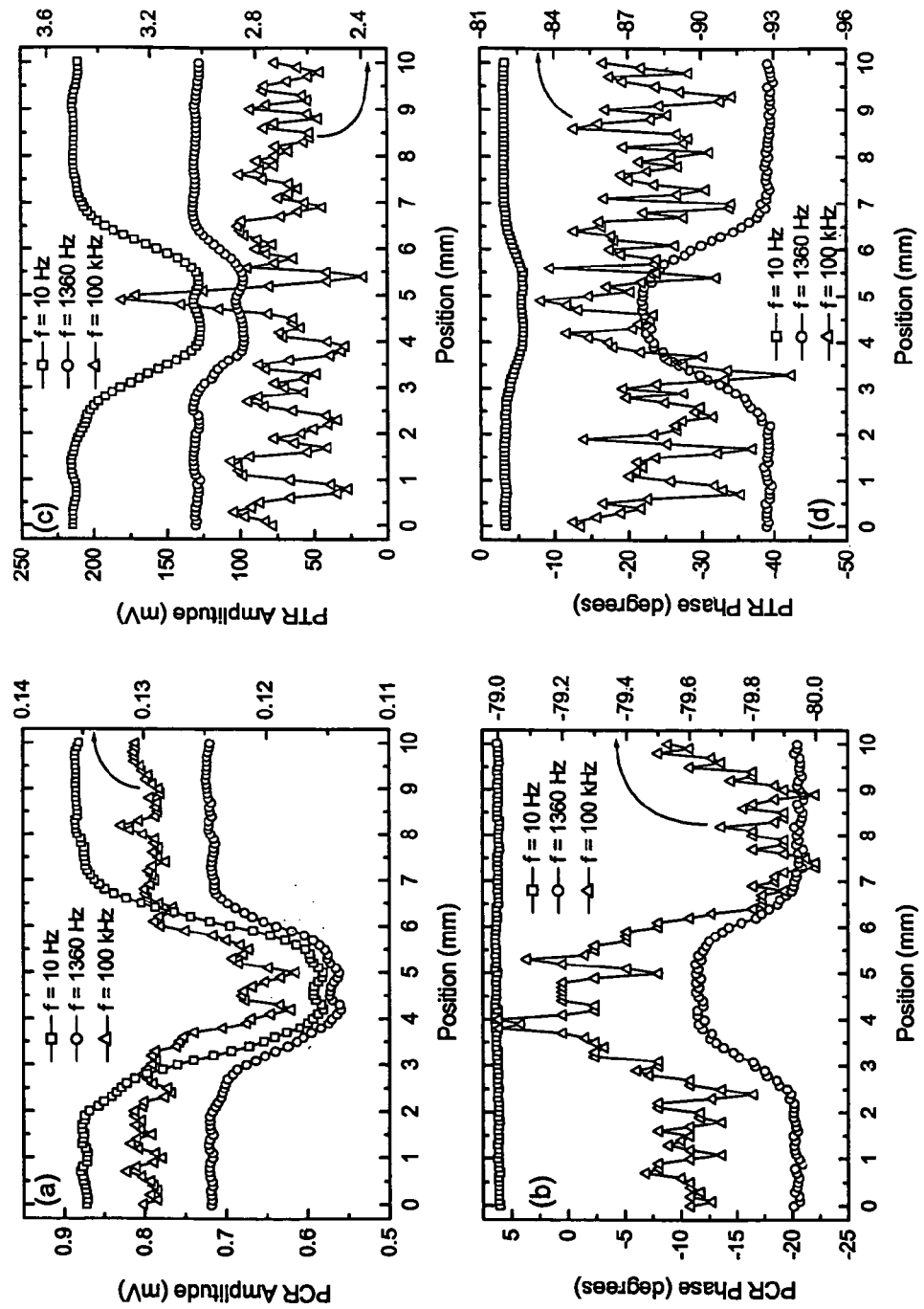
FIG. 10 Line scans over an p-Si wafer region with back-surface mechanical damage. (a) PCR amplitude; (b) PCR phase; (c) PTR amplitude; and (d) PTR phase. The wafer is resting on a mirror support. Laser power: 24 mW.

FIG. 10 shows line scans with the excitation laser beam scanning the front (polished) surface of a 20 Ωcm p-type Si wafer and the IR detector on the same side. Based on the backing results, for maximum signal strength the sample was resting on a mirror. Both PTR and PCR amplitude and phase scans were obtained and both show sensitivity to the deep defect on the back surface scratched region. However, at 100 kHz imaging can be performed only with the PCR signal. At all three selected modulation frequencies, the PCR amplitude decreases when the laser beam scans over the defect region, consistent with the expected CW density decrease as the back-surface defect efficiently traps carriers and removes them from further diffusion and potential radiative recombination. The PCR phase scan remains essentially constant at 10 Hz, FIG. 10b, as the diffusion-wave centroid is solely determined by the ac carrier-wave diffusion length [12]

$$L_{ac}(\omega) = \sqrt{\frac{D*\tau}{1+i\omega\tau}} \qquad (9)$$

where τ is the lifetime and D* is the ambipolar carrier diffusion coefficient. This particular wafer was measured to have τ≅1 ms and D*≅12 cm²/s, which yields an |$L_{ac}$(10 Hz)|≅1.1 mm. Therefore, the CW centroid lies well beyond the thickness of the wafer (~630 μm) and no phase shift can be observed. At the intermediate frequency of 1360 Hz, |$L_{ac}$|≅373 μm, well within the bulk of the wafer. In this case, a phase lead appears within the defective region. This occurs because the CW spatial distribution across the body of the wafer in the defective region is weighed more heavily toward the front surface on account of the heavy depletion occurring at, and near, the back surface. As a result, the CW centroid is shifted toward the front surface, manifested by a phase lead. Finally, at 100 kHz, |$L_{ac}$|≅44 μm. Nevertheless, FIG. 10a shows that there is still PCR amplitude contrast at that frequency, accompanied by a small phase lead, FIG. 10b. For the PTR scans, FIG. 10c shows that the overall amplitude is controlled by the CW component at 10 and 1360 Hz, and there is a small contrast at 100 kHz.

The PTR phase contrast within the region with the back-surface defect first appears as a lag at the lowest frequency of 10 Hz, as expected from a shift away from the front surface of the diffusion-wave centroid in the presence of a remote thermal-wave source which is added to the combined PTR signal. At that frequency the thermal-wave diffusion length [14] is $L_t(\omega)=(2D_t/\omega)^{1/2}\cong 1.7$ mm, that is, the back surface is in thermal conductive communication with the front surface. Therefore, the thermal wave, rather than the carrier wave, controls the overall diffusion-wave PTR behavior of the Si wafer at 10 Hz. At 1360 Hz, however, $L_t\cong 148$ μm, therefore, there is no thermal contact with the back surface. The only signal component affected by the remote defect is the CW, and the phase behaves as in the PCR case, exhibiting a net lead within the defective region. At 100 kHz there is no PTR phase sensitivity to the defect; only a vestigial amplitude contrast, FIGS. 10c,d.

Figure 11:
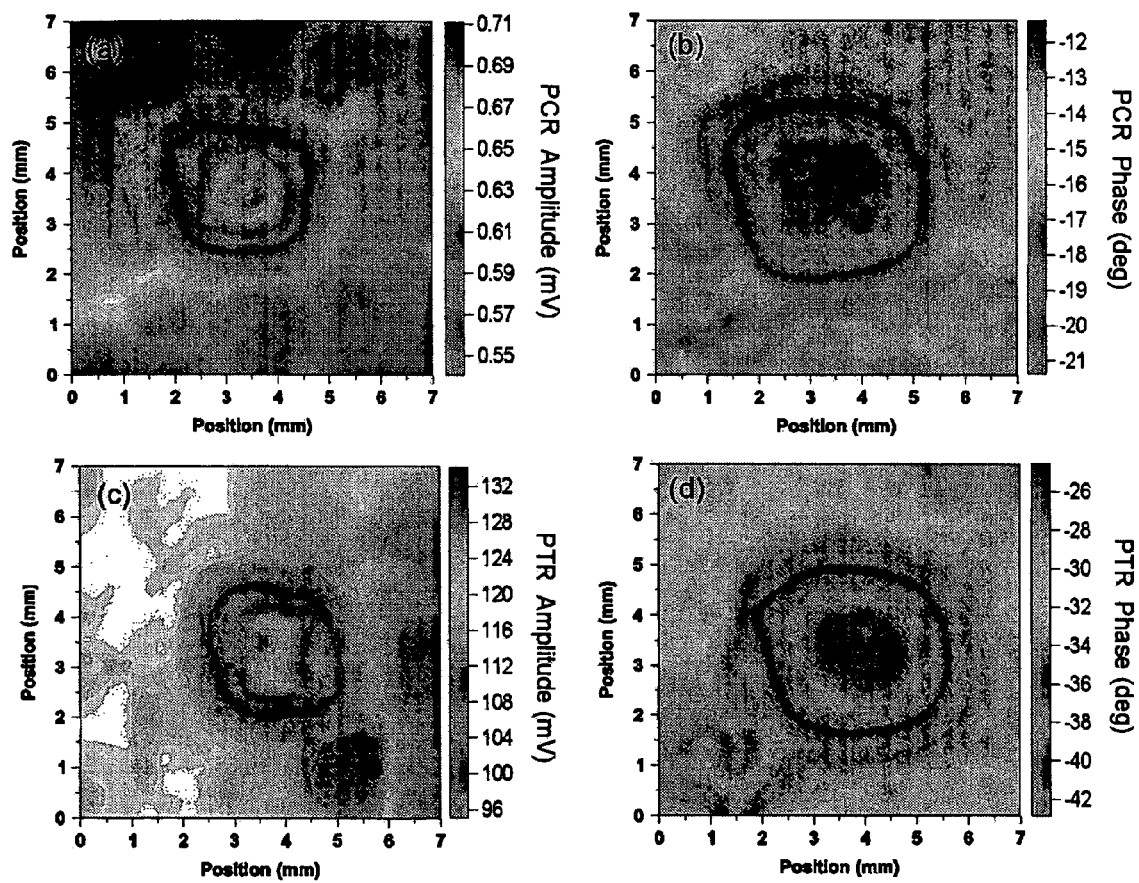
FIG. 11 Scanning imaging of back-surface defect in the p-Si wafer using front-surface inspection. Laser beam radius: 518 μm. Frequency: 1360 Hz. (a) PCR amplitude; (b) PCR phase; (c) PTR amplitude; and (d) PTR phase.
Figure 12:
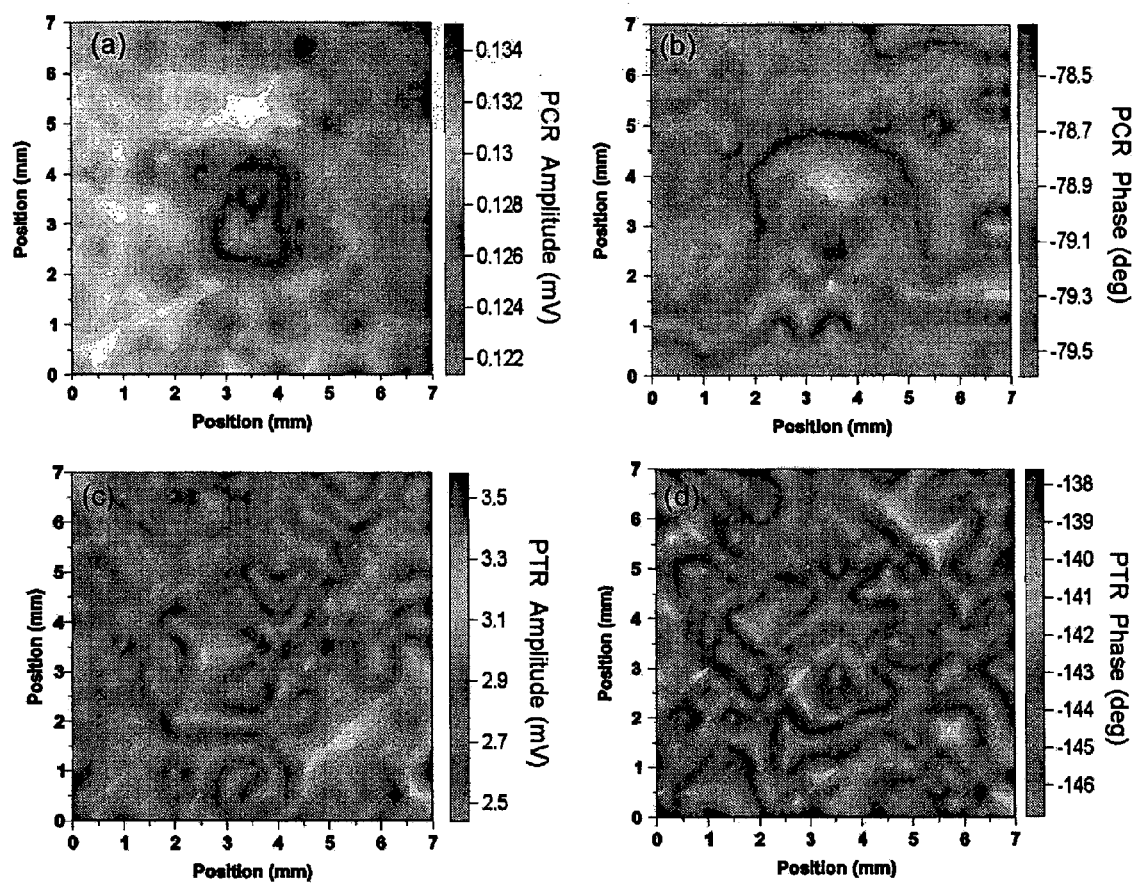
FIG. 12 Scanning imaging of back-surface defect in the p-Si wafer using front-surface inspection. Laser beam radius: 518 μm. Frequency: 100 kHz. (a) PCR amplitude; (b) PCR phase; (c) PTR amplitude; and (d) PTR phase.

To maximize PCR and PTR imaging contrast, differences in amplitudes and phases as a function of frequency were obtained outside and inside the defective region. It is with the help of this type of analysis that the 1360 Hz frequency was chosen for both techniques as one with the highest contrast in phase (but not in amplitude). It is clear that while the PTR contrast is generally higher at low frequencies due to the cooperative trends in both thermal-wave and carrier-wave components, however, PCR imaging contrast becomes superior above ca. 1 kHz and retains its contrast even at the highest frequency of 100 kHz. FIG. 11 shows images of the back-surface defect obtained through front-surface inspection using both techniques at the optimum contrast frequency of 1360 Hz. FIG. 12 shows the same scan at 100 kHz. At this frequency, the PTR image is dominated by noise and is unable to produce any contrast between the intact and defective regions, whereas the PCR image clearly shows the highest spatial resolution of the back-surface defect possible. The PCR phase, FIG. 12b, shows details of the central defect as well as the radially diverging defect structures at the base of the central defect, like a "zoomed in" version of the 1360 Hz image, FIG. 11b. Both PCR images clearly reveal internal sub-structure of the central defect, which was invisible at 1360 Hz.

In a manner reminiscent of conventional propagating wavefields, image resolution increases with decreasing carrier wavelength, $|L_{ac}|$. Similar images to FIGS. 11 and 12 were obtained with air or rubber backing of the same wafer, with marginally diminished detail and contrast. The contrast for PCR imaging at 100 kHz, FIG. 12b, is about 11% for amplitude (FIG. 10a) while the phase difference is only 1° (FIG. 10b). The very high sensitivity of PCR imaging to defect identification is apparent: despite this very small variation in phase, the defect can be clearly delineated. In the case of PTR at 100 kHz, the contrast for amplitude is about 28% (taking the sharp peak in FIG. 10c into account). The phase difference is about 10°. An examination of FIGS. 10c and 10d at 100 kHz shows that this "higher contrast" is caused by fluctuations of the signal, as the PTR signal-to-noise ratio (SNR) is relatively poor, resulting in the disappearance of the back-surface defect from the images FIGS. 12c,d. The PCR images exhibit much higher SNR and clearly reveal the defects structure.

Under front-surface inspection and precise depth profilometric control by virtue of the PCR modulation-frequency-adjustable carrier-wave diffusion length, Eq. (9), FIGS. 11 and 12 show for the first time that with today's high-quality, long-lifetime industrial Si wafers, one can observe full images of sharp carrier-wave density contrast due to underlying defects very deep inside the bulk of a Si wafer. Specifically, high frequency PCR imaging reveals so far unknown very long-range effects of carrier interactions with deep sub-surface defect structures and the detrimental ability of such structures to decrease the overall free photoexcited-carrier density far away from the defect sites at or near the front surface where device fabrication takes place. This phenomenon may be important toward device fabrication improvement through careful selection of substrate wafers with regard to deep bulk growth and manufacturing defects which were heretofore not associated with device performance. Further PCR imaging experiments with shorter lifetime Si wafers have shown that it may be beneficial to use lower quality starting substrates in order to avoid the full effects of deep sub-surface defects on the electronic quality of the upper (device-level) surface.

b) Application to Quantitative Measurements of Electronic Transport Properties

The structure of Eq. (4), the expression for the total emitted power from a semiconductor crystal at the fundamental frequency across the field of view of the IR detector, shows depth dependence of the spatial integrals on the equilibrium IR emission coefficient $\epsilon_o(\lambda)$ of the semiconductor. If this parameter is larger than 1–5 cm$^{-1}$, it introduces a weighting factor $e^{-\epsilon_o(\lambda)z}$ under the integral signs of the compact expression for the total IR emission, Eq. (4), as well as for pure PCR emission, Eqs. (5) and (7). To estimate the effect of such a factor on the PCR signal, especially in the case of low-resistivity, high-residual infrared absorption Si wafers, a simulation was performed using the PCR Eq. (7) in the three-dimensional form $$P(r,\omega;\lambda_1,\lambda_2) \approx \int_{\lambda_2}^{\lambda_1}[1-R_1(\lambda)](1+R_b(\lambda)[1+R_1(\lambda)])\eta_R W_{eR}(\lambda)C(\lambda) \quad (10)$$

$$d\lambda \times \int_0^L \Delta N(r,z,\omega)e^{-\epsilon_o(\lambda)z}dz$$

The equation for $\Delta N(r,z,\omega)$, the 3-D extension of $\Delta N(z,\omega)$ is the solution to the photo-carrier-wave boundary-value problem. It was obtained from Ref. [14], Chap. 9, Eq. (9.106), and it is reproduced here:

$$\Delta N(r,z,\omega) = \quad (11)$$

$$\frac{\eta_Q P_o \alpha}{2\pi h v D^*}\int_0^\infty \frac{e^{-k^2W^2/4}}{(\alpha^2-\xi_e^2)}\left[\left(\frac{G_2g_1-G_1g_2e^{-(\xi_e+\alpha)L}}{G_2-G_1e^{-2\xi_e L}}\right)e^{-\xi_e z} - \right.$$

$$\left. e^{-\alpha z}+\left(\frac{G_2g_1-G_1g_2e^{-(\xi_e+\alpha)L}}{G_2-G_1e^{-2\xi_e L}}\right)e^{-\xi_e(2L-z)}\right]J_o(kr)kdk$$

where (12a)

$$g_1(k) \equiv \frac{D*\alpha+S_1}{D*\xi_e(k)+S_1}; \quad g_2(k) \equiv \frac{D*\alpha-S_2}{D*\xi_e(k)-S_2}$$

with (12b)

$$G_1(k) \equiv \frac{D*\xi_e(k)-S_1}{D*\xi_e(k)+S_1}; \quad G_2(k) \equiv \frac{D*\xi_e(k)+S_2}{D*\xi_e(k)-S_2}$$

and $$\xi_e(k) \equiv \sqrt{k^2+\sigma_e^2} \quad (12c)$$

Here, k stands for the Hankel variable of radial integration, W is the Gaussian laser beam spotsize, $S_1$ and $S_2$ are the front- and back-surface recombination velocities, L is the thickness of the semiconductor slab, $\alpha$ is the optical absorption coefficient at the excitation wavelength $\lambda_{vis}=c_o/v$. $\eta_Q$ is the quantum yield for optical to electronic energy conversion and $P_o$ is the laser power. The carrier wavenumber is defined as $$\sigma_e(\omega) \equiv \sqrt{\frac{1+i\omega\tau}{D^*\tau}} = \frac{1}{L_{ac}(\omega)} \quad (13)$$

In the simulations that follow and in the theoretical fits to the experimental data, the variable r was integrated over the surface of the IR detector [4].

Figure 13:
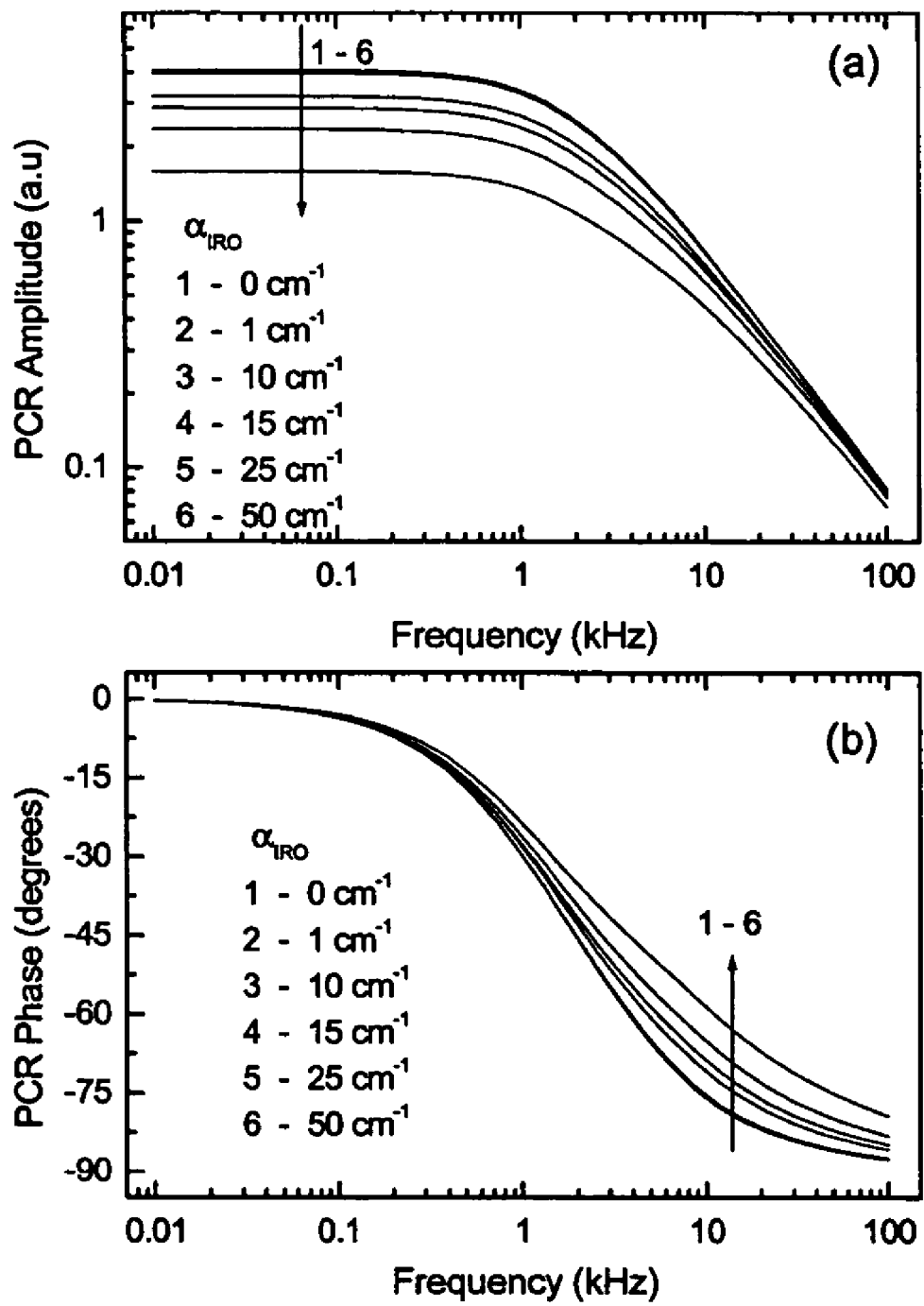
FIG. 13 Simulations of PCR signal frequency dependence in p-Si with the residual IR absorption coefficient as a parameter. (a) Amplitude; (b) phase. $\lambda = 514$ nm, beam radius $w = 518$ μm, detector radius $= 563$ μm, wafer thickness $= 675$ μm; $\tau = 1$ ms; $D^* = 15$ cm$^2$/s, $S_1 = 100$ cm/s, $S_2 = 300$ cm/s.

FIG. 13 shows simulations of the PCR frequency dependence for p-Si of (what amounts to) different resistivity with the equilibrium IR absorption coefficient as a IR-wavelength-independent (average) parameter. From Kirchhoff's law, $\epsilon_o = \alpha_{IRo}$. The curves show a decrease in amplitude, especially at low frequencies, in the carrier-diffusion-wave thin regime ($|L_{ac}(\omega)|>L$), as emissions throughout the bulk of the crystal are gradually impeded with increasing background carrier density (and thus IR absorption coefficient) due to self-absorption of the IR recombination photons by the background free carrier-wave density. At high frequencies, in the carrier-diffusion-wave thick regime ($|L_{ac}(\omega)|<<L$), little attenuation of the backward emitted IR recombination photon flux occurs because the IR-opaque subsurface layer involved in the CW-generated emission is very thin. Therefore, all amplitude curves converge. PCR phase lags show sensitivity at high frequencies; they decrease with increasing frequency because the contributing CW centroid moves closer to the front surface with increasing IR opacity of the semiconductor. FIG. 13 shows that for typical $\alpha_{IRo}$ ranges of 1–2 cm$^{-1}$ [32] the effect of self-reabsorption of IR photons due to background free carrier-wave densities is minimal and therefore the approximate Eqs. (4), (5), (7), and (8) are justified.

The PCR image contrast of FIGS. 11 and 12 can, in principle, be quantified by use of the CW term in Eq. (7), appropriately modified to accommodate the defective region:

$$\Delta P(\omega) \approx F_2(\lambda_1, \lambda_2) \left[ \int_0^L \Delta N(z, \omega) dz - \int_0^L \Delta N_d(z, \omega) dz \right] \quad (14)$$

where $\Delta P(\omega)$ is the difference in signal between the intact and defective regions. This is a complex quantity, so it can be separated out into amplitude and phase components. The apparent simplicity of this expression is due to the fact that the sub-surface defects considered here are on the back surface of the wafer and their presence mostly impacts the value of $S_2$ in Eq. (11), while the bulk parameters and the terms comprising the prefactor $F(\lambda_1,\lambda_2)$, Eq. (8), remain essentially unaltered, including $C_d(\tau) \approx C(\lambda)$ for a thin damage layer in an otherwise homogeneous semiconductor. If these conditions are not fulfilled, then a more complete expression of the carrier recombination related emissions must be used to quantify PCR contrast due to distributed sub-surface electronic defect structures.

Figure 14:
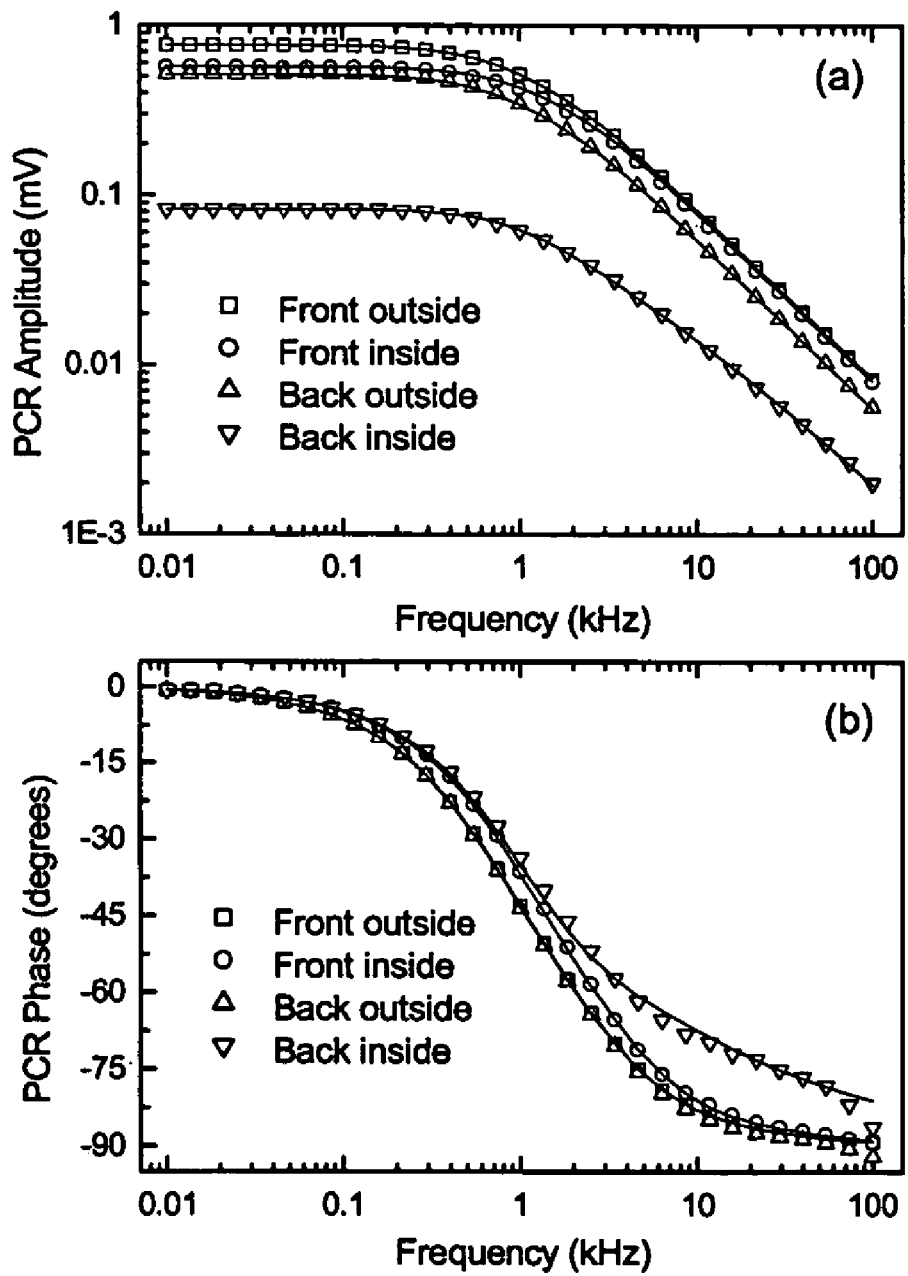
FIG. 14 Front- and back-surface PCR frequency scans inside and outside a defect area of a p-Si wafer on aluminum backing. Detector: InGaAs; beam size: 1.4 mm; Ar-ion laser power: 20 mW. (a) Amplitudes and (b) phases. Best fit parameters.

The mild mechanical defect on the back surface of the p-type Si wafer that generated the images of FIGS. 11 and 12 proved to be too severe for our sensitive InGaAs photodetector: upon scanning the affected surface the PCR signal vanished within the region of the defect, apparently due to the highly efficient trapping of the photogenerated free carriers by the high density of near-surface electronic defect states. Therefore, a different region of the same wafer was chosen to create a visually undetectable defect by simply touching the back surface of the wafer with paper. Then both PCR frequency scans were performed on both sides of the material, outside and inside the defect region. FIG. 14 shows the PCR frequency scan amplitudes and phases for all four spots, as well as theoretical fits to the experimental data. The signal normalization was performed by extracting the CW component of the PTR signal, i.e. the depth integral over $\Delta N(r,z,\omega)$, Eq. (11), associated with the prefactor $C_p$ in the front intact region, and making it the reference PCR signal for the same region. The thus obtained PCR amplitude and phase transfer functions were subsequently used for all other measurements. The D* values those outside the defect remain constant for both sides of the wafer, however, the D* value from the back inside the defect region is relatively low.

The higher sensitivity of the InGaAs detector to the electronic state of the inspected surface is probably responsible for this discrepancy, as the theoretical phase fit is poor at high frequencies (>1 kHz) within that region, an indication of near-surface depth inhomogeneity of transport properties. FIG. 14 and the resultant theoretical fits show that PCR signals are very sensitive to the electronic state of the probed semiconductor surface and bulk. The ability to measure the diffusion coefficient D* also allows for the calculation of the conductivity mobility, $\mu$, through the use of the Einstein relation $D=(kT/q)\mu$ where k is the Boltzmann constant, T is the temperature, and q is the elementary charge. The measured conductivity mobility of a n-type silicon wafer with resistivity $\rho=10-15$ $\Omega$cm, $N \sim 8 \times 10^{14}$ cm$^{-3}$, and a 980 angstrom thermally grown oxide layer is presented in FIG. 15. The temperature dependence of the conductivity mobility was found to have a relationship similar to that measured using electrical techniques [33].

In an embodiment of the method the semiconductor material is suitably and rapidly heated by a contacting thermal source and the PCR signal (controlled by the thermal emissions from the recombination-induced infrared emission) is monitored at a suitable PCR frequency such that thermal emissions occur from a defect or impurity state in the material produce a peak in the temperature scan when the material temperature is such that the thermal energy forces trapped carriers to evacuate their trap states at a rate simply related to the PCR frequency. In this manner the energy of the impurity or defect deep level is extracted from the PCR peaks in a series of temperature scans at fixed frequencies using a simple Boltzmann factor, and the PCR signal magnitude is a measure of the occupation density of the level. Alternatively, the PCR frequency is scanned for different (fixed) temperatures and the energy of the level is obtained from an Arrhenius plot of the logarithm of the (modulation period $P_{max}$ of the lock-in in-phase signal where a PCR peak occurs at each temperature $T_j$ times $T_j^2$) vs. $1/T_j$. This metrology method can be suitably called PCR Deep-Level Thermal Spectroscopy and can be used for identification of electronic impurity species and/or contamination ions and for estimating their concentration in a semiconductor.

c) Application to Ion Implant Dose Monitoring in Silicon

The demonstrated sensitivity to surface defects [19] allows for the use of PCR to monitor ion implant dose. FIG. 16 shows the PCR amplitude dependence as a function of dose for (100) oriented p-type silicon wafers with a thermally grown oxide layer of 200 Å implanted at room temperature at an angle of 7° to suppress channelling with fluences from $10^{10}$ to $10^{16}$ cm$^{-2}$ with the following species and energy combinations: $^{11}$B$^+$(10 keV, 50 keV, 180 keV), $^{75}$As$^+$(80 keV, 150 keV), $^{31}$P$^+$(30 keV, 80 keV, 285 keV) and BF$_2^+$(30 keV, 50 keV). Inspection of FIG. 16(a) through (d) shows that the PCR signal dependence on dose can be broken down roughly into four regions with the actual dose defining the transition of each region depending on the mass of the implanted ion. In region I the amplitude decreases rapidly with increasing dose as the degree of damage to the lattice structure increases and electronic integrity of the surface region is compromised resulting in carrier trapping, increased surface recombination velocities, and decreased diffusivities and lifetimes. In region 11 the electronic sensitivity to dose begins to saturate and the PCR amplitude decreases slightly as the size of the damaged region increases with dose [34]. The production of amorphous phase Si brings the onset of sensitivity to the optical properties in Region III resulting in another dose range of rapidly decreasing amplitude as the absorption coefficient increases and results in a greater percentage of the photogenerated carriers being created in a region of compromised electronic integrity. For the more massive $As^+$ implants a fourth region is visible as the onset of optical saturation occurs near $10^{16}$ $cm^{-2}$ and the PCR sensitivity to dose again experiences a rapid decline. Saturation of the electrical sensitivity prior to the onset of the optical sensitivity is a result of the dependence of the carrier-diffusion-wave on electrical percolation paths and the dependence of the optical properties of the sample on relatively large volumes [35].

A key feature of the results presented in FIG. 16 is the monotonic behavior over a large range of implant dose. The only exceptions for the wafers studied were the $B^+$ and $P^+$ implanted samples that exhibited slightly non-monotonic behavior in the $5 \times 10^{12}$ to $10^{13}$ $cm^{-2}$ region at intermediate energy levels and the $As^+$ implanted samples that had non-monotonic behaviour above $5 \times 10^{15}$ $cm^{-2}$. This monotonic behaviour is an advantage over photothermal techniques such as photomodulated reflectance which exhibit non-monotonic signals over this dose range due to the competing thermal-wave and carrier-wave components that generate them [37]. Several other features of note in FIG. 16 are the PCR dependence on energy and on excitation wavelength. In general, the PCR amplitude decreases with implant energy as the depth of the damaged region increases and consumes a greater portion of the photo-generation volume. Similarly, for a given energy, the PCR amplitude decreases with the excitation wavelength as the increasing absorption coefficient results in a photo-generation volume closer to the implanted region. Both of these phenomena are the result of a modification of the weighting of the contributions to the PCR signal from the (damaged) surface region and the bulk of the sample [38, 39]. This increased dependence on the damaged region of the sample results in an increasing sensitivity of the PCR signal to dose with decreasing absorption depth (i.e. wavelength) of the excitation source [40].

ii) Interferometric Photocarrier Radiometry a) Description of the Method

All previous photothermal and optical approaches to characterizing semiconductors have been based a single excitation source focused onto one surface of the sample. This results in a baseline signal from the homogeneous bulk that can be large relative to the contrast signal (i.e. signal variation) from any inhomogeneities. Recently, two approaches have been taken in efforts to eliminate this baseline signal from photothermal experiments in order to improve the sensitivity of the instrument.

A purely thermal-wave interferometric approach has been applied to photo-pyroelectric measurements of trace gas elements [41,42]. Also, the introduction of a dual-pulse wave form into a single excitation beam has been used to create a differential technique that amounts to a common-mode reject scheme [43,44]. Both approaches have shown that suppression of the baseline signal improves the sensitivity and dynamic range compared to the conventional single-ended equivalent. The double-ended interferometric invention, while similar in principle to the PPE interferometric approach, is a completely novel approach to the characterization of solid-state samples, and in particular semiconductors, relying on the interference of the separately generated carrier-density waves in the sample as opposed to other suggested photothermal interferometric techniques which utilize the interference patterns of optical beams interacting with the sample [45].

The instrumentation for interferometric PCR of a semiconductor sample is described above with respect to FIG. 4. Two laser beams modulated at identical frequencies with one phase shifted 180 degrees with respect to the other are focused onto opposite sides of the sample to generate two separate carrier-density waves. The PCR signal is described by equation (10) with the carrier density $\Delta N(r,z,\omega)$ being the solution to the photo-carrier-wave boundary-value problem similar to equation (11) but with two excitation sources. The intensity of the laser focused on the front surface of the sample is adjusted to ensure destructive interference of the two waves and thus a zero baseline signal. As the wafer is scanned laterally any inhomogeneities or defects present in the material alter the diffusion of one or both of the photo-generated carrier density waves which no longer interfere destructively and thus produce a non-zero signal. This approach of using a zero baseline signal improves the dynamic range of the instrument and the sensitivity to inhomogeneities and thus provides enhanced imaging contrast of lateral contamination or other inhomogeneities compared to the single-ended PCR.

From these scans, maps can be produced of any inhomogeneities or defects that affect carrier density, either by enhancing recombination or altering diffusion coefficients. The theoretical model includes an effective carrier diffusion model to obtain quantitative values for the electronic and transport parameters, and combining quantitative results of the theoretical model with maps produced from spatially scanning across at least one surface of the material to provide quantitative imaging of the material. Besides the theoretical fits, maps produced from scanning at least one surface of the material can be combined with calibration curves to provide quantitative imaging of the material. The calibration curves are obtained by measuring the PCR signal from reference samples with known composition, structure and material properties. The calibration curves allow for direct correlation between the PCR signals and the material property and/or industrial process to be monitored.

This approach of using a zero baseline signal improves the dynamic range of the instrument and the sensitivity to inhomogeneities and thus provides enhanced imaging contrast of lateral contamination or other inhomogeneities compared to the single-ended PCR.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

[1]. A. Mandelis, R. Bleiss and F. Shimura, J. Appl. Phys. 74, 3431 (1993).
[2]. A. Mandelis, A. Othonos, C. Christofides and J. Boussey-Said, J. Appl. Phys. 80, 5332 (1996).
[3]. A. Othonos, C. Christofides and A. Mandelis, Appl. Phys. Lett. 69, 821 (1996).
[4]. T. Ikari, A. Salnick and A. Mandelis, J. Appl. Phys. 85, 7392, (1999).
[5]. M. E. Rodriguez, A. Mandelis, G. Pan, L. Nicolaides, J. A. Garcia and Y. Riopel, J. Electrochem. Soc. 147, 687, (2000).
[6]. A. Mandelis and Y. Riopel, J. Vac. Sci. Technol. A 18, 705, (2000).
[7]. M. E. Rodriguez, A. Mandelis, G. Pan, J. A. Garcia, V. Gorodokin and Y. Raskin, J. Appl. Phys. 87, 8113, (2000).
[8]. A. Mandelis, M. E. Rodriguez, Y. Raskin and V. Gorodokin, Phys. Stat. Sol. (a) 185, 471, (2001).
[9]. M. E. Rodriguez, A. Mandelis, G. Pan, J. A. Garcia and Y. Riopel, Solid-State Electron. 44, 703, (2000).
[10]. N. Mikoshiba and K. Tsubouchi, in Photoacoustic and Thermal-Wave Phenomena in Semiconductors (A. Mandelis, Ed., North-Holland, N.Y., 1987), Chap. 3; C. Christofides, A. Othonos and K. Kalli, Electrochem. Soc. Proc. 29, 153 (2001).
[11]. A. Mandelis, R. A. Budiman, M. Vargas and D. Wolff, Appl. Phys. Lett. 67, 1582 (1995).
[12]. A. Mandelis, Solid-State Electron. 42, 1, 1998.
[13]. C. Christofides, M. Nestoros and A. Othonos, in Semiconductors and Electronic Materials, Progress in Photoacoustic and Photothermal Phenomena Vol. IV (A. Mandelis and P. Hess, Eds., SPIE, Bellingham, Wash., 2000), Chap. 4.
[14]. A. Mandelis, "Diffusion-Wave Fields: Mathematical Methods and Green Functions", Springer-Verlag, N.Y., (2001); Chap. 9.
[15]. R. E. Wagner and A. Mandelis, Semicond. Sci. Technol. 11, 300 (1996).
[16]. A. Salnick, A. Mandelis, H. Ruda and C. Jean, J. Appl. Phys. 82, 1853 (1997).
[17]. S. J. Sheard, M. G. Somekh and T. M. Hiller, Mater. Sci. Eng. B 5, 101 (1990).
[18]. A. Rosencwaig, in Photoacoustic and Thermal-Wave Phenomena in Semiconductors (A. Mandelis, Ed., North-Holland, N.Y., 1987), Chap. 5.
[19]. A. Mandelis, J. Batista, and D. Shaughnessy, Phys. Rev. B 67, 205208 (2003).
[20]. A. Mandelis, A. Salnick, L. Chen, J. Opsal and A. Rosencwaig, J. Appl. Phys. 85, 1811 (1999).
[21]. R. E. Wagner and A. Mandelis, Semicond. Sci. Technol. 11, 289 (1996); and 11, 300 (1996).
[22]. A. Mandelis and R. E. Wagner, Jpn. J. Appl. Phys. 35, 1786 (1996).
[23]. R. N. Hall, Inst. Electr. Eng. 106 B, Suppl. No 17, 923 (1959).
[24]. W. van Roosbroeck and W. Shockley, Phys. Rev. 94, 1558 (1954).
[25]. G. Kirchhoff, Abhandlungen über Emission und Absorption (M. Planck, Ed., Verlag von Wilhelm Engelmann, Leipsig, 1898), pp. 11–36.
[26]. A. Mandelis, unpublished.
[27]. R. A. Smith, Semiconductors 2nd Ed. (Cambridge Univ. Press, Cambridge, 1978), pp. 118–119.
[28]. Judson Technologies Detector Offerings; wwwjudtech.com.
[29]. R. D. Tom, E. P. O'Hara and D. Benin, J. Appl. Phys. 53, 5392 (1982).
[30]. M. E. Rodriguez, J. A. Garcia, A. Mandelis, C. Jean and Y. Riopel, Appl. Phys. Lett. 74, 2429 (1999).
[31]. S. J. Sheard and M. G. Somekh, Electron. Lett. 23, 1134 (1987).
[32]. F. A. Johnson, Proc. Phys. Soc. (London) 73, 265 (1959).
[33]. J. Batista, A. Mandelis, and D. Shaughnessy, Appl. Phys. Lett. 82, 4077 (2003).
[34]. S. Prussin, D. I. Margolese, and R. N. Tauber, J. Appl. Phys. 54, 2316 (1983).
[35]. CH. Wilbertz, K. L. Bhatia, W. Krätschmer and S. Kalbitzer, Mat. Sci. Eng. B 2, 325 (1989).
[36]. B. Li, D. Shaughnessy, A. Mandelis, J. Batista, and J. Garcia, submitted to J. Appl. Phys December 2003.
[37]. A. Salnick and J. Opsal, Rev. Sci. Instr 74, 545 (2003).
[38]. D. Shaughnessy and A. Mandelis, J. Appl. Phys. 93, 5244 (2003).
[39]. A. Othonos and C. Christofides, Nuclear Instr. Meth. Physics Research B117, 367 (1996).
[40]. D. Shaughnessy, B. Li, A. Mandelis, and J. Batista, submitted to Appl. Phys Lett. December 2003).
[41]. C. Wang and A. Mandelis, J. Appl. Phys. 85, 8366 (1999).
[42]. C. Wang and A. Mandelis, Rev. Sci. Instr. 71, 1961 (2000).
[43]. A. Mandelis, S. Paoloni, and L. Nicolaides, Rev. Sci. Instr. 71, 2440 (2000).
[44]. S. Paoloni, L. Nicolaides, and A. Mandelis, Rev. Sci. Instr. 71, 2445 (2000).
[45]. see for example: H. G. Walther et al., Appl. Phys. Lett. 57, 1600 (1990).

Therefore what is claimed is:

1. A non destructive method for characterizing electronic properties of materials, comprising the steps of:
   (a) irradiating at least one surface of a material with an energy beam output from a modulated or pulsed excitation source wherein a recombination-induced infrared emission is responsively emitted from the material;
   (b) filtering Planck-mediated thermal emissions from the recombination-induced infrared emission to produce a filtered recombination-induced infrared emission;
   (c) detecting said filtered recombination-induced infrared emission; and
   (d) calculating selected electronic properties of the material by one of
   i) fitting the detected filtered recombination-induced infrared emission to a theoretical model of the photocarrier response of the irradiated material to calculate selected properties of the material, and
   ii) using suitable calibration charts or tables to extract selected electronic properties of the material by comparison of the detected filtered recombination-induced infrared emission with reference detected filtered recombination-induced infrared emissions from reference materials with known properties.

2. The method according to claim 1 wherein the step of irradiating at least one surface of the material with an energy beam includes irradiating one surface of the material which generates a carrier-density wave in the material which upon recombination generates the recombination-induced infrared emission.

3. The method according to claim 2 including focussing the energy beam to a pre-selected size on at least one surface, and spatially scanning the focussed energy beam laterally across at least one surface of the material and calculating therefrom maps of any inhomogeneities or defects that affect carrier density, either by enhancing recombination or altering diffusion coefficients, and wherein the theoretical model includes an effective carrier diffusion model to obtain quantitative values for the selected properties of the material, and combining quantitative results of the theoretical model with maps produced from spatial scanning across at least one surface of the material to provide quantitative imaging of the material.

4. The method according to claim 3 wherein the selected properties calculated from the theoretical model include carrier recombination lifetime, $\tau$, carrier diffusivity, D, surface recombination velocities, S, carrier diffusion lengths, L, and carrier mobility, $\mu$, and space charge layer width, W.

5. The method according to claim 4 wherein the excitation source is a laser modulated at a modulation frequency, including scanning the modulation frequency in a pre-selected range, and wherein the theoretical model includes an effective carrier diffusion model to calculate the selected properties of the material irradiated with a modulated laser, and combining quantitative results of the theoretical model with maps produced from spatially scanning across at least one surface of the material to provide quantitative imaging of the material.

6. The method according to claim 4 wherein the excitation source is a laser pulsed for a given time duration, including scanning the time duration of the pulses in a pre-selected range, and wherein the theoretical model includes an effective carrier diffusion model to calculate the selected properties of the material irradiated with a pulsed laser, and combining quantitative results of the theoretical model with maps produced from spatially scanning across at least one surface of the material to provide quantitative imaging of the material.

7. The method according to claim 4 wherein the maps produced from scanning at least one surface of the material is combined with calibration curves to provide quantitative imaging of the material.

8. The method according to claim 1 wherein the step of irradiating the material with an energy beam includes irradiating a first surface of the material with a first energy beam to generate a first carrier-density wave and irradiating a second surface of the material opposed to the first surface of the material with a second energy beam to generate a second carrier-density wave with the first and second energy beams being output from optical excitation sources modulated at identical frequencies with the second energy beam having a phase lag of 180 degrees with respect to the first energy beam, and wherein the intensity of the first excitation source focused on the first surface of the material is adjusted to ensure destructive interference of the two carrier-density waves and to give a zero baseline signal.

9. The method according to claim 8 including scanning the first and second energy beams laterally across the material, or moving the material between the first and second energy beams, and detecting for non-zero signals, wherein any inhomogeneities or defects present in the material alter the diffusion, either by enhancing recombination or altering diffusion coefficients, of one or both of the photogenerated carrier density waves which no longer interfere destructively and thus produce a non-zero signal, and calculating therefrom maps of any inhomogeneities or defects that affect carrier density, and wherein the theoretical model includes an effective carrier diffusion model to obtain quantitative values for the selected properties of the material, and combining quantitative results of the theoretical model with maps produced from spatially scanning across at least one surface of the material to provide quantitative imaging of the material.

10. The method according to claim 9 wherein the selected properties calculated from the theoretical model include carrier recombination lifetime, $\tau$, carrier diffusivity, D, surface recombination velocities, S, carrier diffusion lengths, L, and carrier mobility, $\mu$, and space charge layer width, W.

11. The method according to claim 9 wherein the excitation source is a laser modulated at a modulation frequency, including scanning the modulation frequency in a pre-selected range, and wherein the theoretical model includes an effective carrier diffusion model to calculate the selected properties of the material irradiated with a modulated laser, and combining quantitative results of the theoretical model with maps produced from spatially scanning across at least one surface of the material to provide quantitative imaging of the material.

12. The method according to claim 9 wherein the excitation source is a laser pulsed for a given time duration, including scanning the time duration of the pulses in a pre-selected range, and wherein the theoretical model includes an effective carrier diffusion model to calculate the selected properties of the material irradiated with a pulsed laser, and combining quantitative results of the theoretical model with maps produced from spatially scanning across at least one surface of the material to provide quantitative imaging of the material.

13. The method according to claim 9 wherein the maps produced from scanning at least one surface of the material is combined with calibration curves to provide quantitative imaging of the material.

14. The method according to claim 1 wherein the excitation source is an optical excitation source pulsed in time domain.

15. The method according to claim 1 wherein the excitation source is an optical excitation source modulated in frequency domain.

16. The method according to claim 1 wherein said excitation source is a laser.

17. The method according to claim 16 wherein the laser is a solid state laser.

18. The method according to claim 17 wherein said solid state laser is modulated by current modulation.

19. The method according to claim 16 wherein the laser is a gas laser.

20. The method according to claim 1 wherein the excitation source is one of an electron beam source, a flashlamp, a light emitting diode (LED), or any other electromagnetic wave source, which produces a photon beam having sufficient energy to excite carriers in the semiconductor or optical material.

21. The method according to claim 1 wherein the excitation source is modulated by one of a mechanical chopper, an acousto-optic modulator and an electro-optic modulator.

22. The method according to claim 1 wherein the excitation source is a pulsed laser with short duration optical pulses triggered by an internal or external electronic control circuit.

23. The method according to claim 1 wherein the step of detecting the emitted recombination-induced infrared emission is accomplished using one of a room temperature solid state detector, a cooled solid state detector.

24. The method according to claim 1 wherein the step of detecting the emitted recombination-induced infrared emission includes using an imaging array sensor to rapidly image a large surface area of the surface of the material.

25. The method according to claim 1 wherein the step of filtering Planck-mediated thermal emissions from the recombination-induced infrared emission is accomplished using a coated optical window made of material transparent in the spectral range of about 1–3 microns.

26. The method according to claim 1 wherein the step of filtering is accomplished using a solid state detector with detectivity spectrum suitable for eliminating any sensitivity to the incident optical source radiation and to the Planck-mediated thermal emissions while retaining sufficient detectivity in the spectral range of 0.7–3 microns, or another spectral range suitable for semiconductors of higher or lower bandgap energies than that of silicon wafers.

27. The method according to claims 26 wherein the material includes at least one oxide layer, and wherein one of the selected electronic properties includes calculating a space charge layer width formed by charge concentration in the oxide layer which can be used to calculate a charge concentration and degree of band-bending at the oxide-semiconductor interface, using a suitable theoretical model.

28. The method according to claims 26 wherein the non destructive optical method for characterizing electronic properties of materials is performed on production line in which the material is processed into a product.

29. The method according to claim 28 wherein the material is a semiconductor, and wherein the production line is a semiconductor wafer production line or a semiconductor chip fabrication line.

30. The method according to claim 1 wherein the material is selected from the group consisting of semiconductor materials, optical materials and luminescent materials.

31. The method according to claim 30 wherein the energy beam has an energy equal to or greater than a bandgap energy for raising electrons from a valence energy band to a conduction band for producing photo-generated carriers in the semiconductor material or the optical material.

32. The method according to claim 30 wherein the energy beam has an energy equal to or greater than an energy difference between an energy of a bottom of a conduction band and energy levels in a bandgap associated with dopants, impurity atoms or defects for raising electrons from said energy levels in the bandgap to said conduction energy band for producing photo-generated carriers in the semiconductor material or excited quantum states in the optical material.

33. The method according to claim 30 wherein the semiconductor material includes a scribeline structure on a processed wafer separating device and chip arrays, and wherein probing along the scribeline obtains measurements of signal levels which depend on minority-carrier recombination lifetimes.

34. The method according to claim 30 wherein the semiconductor material includes a layered epitaxial structure, and wherein a dopant uniformity and concentration of the layered epitaxial structure is monitored.

35. The method according to claim 30 wherein the semiconductor material includes ion implanted dopants, and wherein implantation parameters including energy, dose and junction depth can be measured by either fitting the emitted signals to suitable theoretical models or through use of calibration curves.

36. The method according to claim 30 wherein the semiconductor material includes heavy metal contamination, and wherein the contamination can be measured qualitatively by suitable signal contrast between contaminated and uncontaminated regions or quantitatively by either fitting the emitted signals to appropriate theoretical models or through use of calibration curves.

37. The method according to claim 30 wherein the semiconductor material include p-n junction devices formed therein or oxide-semiconductor interfaces.

38. The method according to claim 1 wherein the material is placed on an effective backing material to enhance the recombination-induced infrared emission from the material.

39. The method according to claim 38 wherein the backing material is an infrared reflector material.

40. The method according to claim 1 wherein the excitation source is modulated at a pre-selected modulation frequency, including heating the material suitably and rapidly wherein the detected filtered recombination-induced infrared emission is monitored at the pre-selected modulation frequency such that thermal emissions occurring from a defect or impurity state in the material produce a peak in a temperature scan when the material temperature is such that the thermal energy due to heating the material forces trapped carriers to evacuate their trap states at a rate simply related to the pre-selected modulation frequency, and wherein the energy of the impurity or defect deep level is extracted from the PCR peaks in a series of temperature scans at fixed frequencies using a simple Boltzmann factor, and the PCR signal magnitude is a measure of the occupation density of the level.

41. The method according to claim 1 wherein the excitation source is modulated at a pre-selected modulation frequency, wherein the detected filtered recombination-induced infrared emission is monitored at a pre-selected temperature and the frequency is scanned, wherein thermal emissions occurring from a defect or impurity state in the material produce a peak in the frequency scan when the modulation frequency is approximately equal to a rate of forcing trapped carriers to evacuate their trap states at the pre-selected temperature, and wherein, the pre-selected modulation frequency is scanned for different (fixed) temperatures and an energy of the level is obtained from an Arrhenius plot of modulation period times $T_{max}^2$ vs. $1/T_{max}$ using the temperature values, $T_{max}$, of the thermal-emission-induced PCR infrared emission peak occurring at each frequency scan.

42. An apparatus for non destructive characterization of electronic properties of materials, comprising;
  a) excitation source means for irradiating at least one surface of a material with energy beams from the optical excitation source means wherein a recombination-induced infrared emission is responsively emitted from the material, the excitation source means being a modulated or pulsed optical excitation source means;
  b) filtering means for filtering Planck-mediated emissions from the recombination-induced infrared emission to produce a filtered recombination-induced infrared emission;
  c) detection means for detecting the filtered recombination-induced infrared emission;
  d) processing means for one of
  i) fitting the detected filtered recombination-induced infrared emission to a theoretical model of the photo-carrier response of the irradiated material to calculate selected properties of the material, and
  ii) comparing the detected filtered recombination-induced infrared emission with reference detected filtered recombination-induced infrared emissions from reference materials with known properties.

43. The apparatus according to claim 42 including means for heating the sample suitably and rapidly wherein the detected filtered recombination-induced infrared emission is monitored at a suitable frequency such that thermal emissions occuring from a defect or impurity state in the material produce a peak in the temperature scan when the material temperature is such that the thermal energy forces trapped carriers to evacuate their trap states at a rate simply related to the suitable frequency, and wherein the energy of the level of the defect or impurity state is obtained from an Arrhenius plot of the lifetime times $T^2$ vs. $1/T$ using the temperature values of the PCR peaks at each frequency.

44. The apparatus according to claim 43 wherein the selected properties calculated from the theoretical model include carrier recombination lifetime, $\tau$, carrier diffusivity, D, surface recombination velocities, S, carrier diffusion lengths, L, and carrier mobility, $\mu$, and space charge layer width, W.

45. The apparatus according to claim 42 including focussing means for focussing the energy beam to a pre-selected spot size on the at least one surface, and including spatial scanning means for spatially scanning the focussed energy beam across the at least one surface of the material, and wherein the theoretical model calculates from the spatial scans maps of any inhomogeneities or defects that affect carrier density, either by enhancing recombination or altering diffusion coefficients, and wherein the theoretical model includes an effective carrier diffusion model to obtain quantitative values for the selected properties of the material, and wherein the processing means combines quantitative results from the theoretical model or calibration curves with the maps to provide quantitative imaging of the material.

46. The apparatus according to claim 45 wherein the selected properties calculated from the theoretical model include carrier recombination lifetime, $\tau$, carrier diffusivity, D, surface recombination velocities, S, carrier diffusion lengths, L, and carrier mobility, $\mu$, and space charge layer width, W.

47. The apparatus according to claim 42 wherein the excitation source means for irradiating at least one surface of a material with an energy beam includes means for irradiating two opposed surfaces of the material for producing a first energy beam irradiating a first side of the material to generate a first carrier-density wave in the material and for a producing a second energy beam irradiating a second surface of the material opposed to the first surface of the material to generate a second carrier-density wave in the material, with the first and second energy beams being focussed onto the same position but from opposite sides of the material so that the first and second carrier waves generated in the material are aligned opposite to each other, including modulation means for modulating the first and second energy beams at substantially identical frequencies with the second energy beam having a phase lag of 180 degrees with respect to the first energy beam, and including intensity adjustment means for adjusting an intensity of the first energy beam focused on the first surface of the material to ensure destructive interference of the two carrier-density waves and to give a substantially zero baseline signal.

48. The apparatus according to claim 47 including focussing means for focussing the first and second energy beams to a pre-selected spot size on the first and second opposed surfaces, and including scanning means for scanning the first and second energy beams laterally across the material, or moving the material between the first and second energy beams, and wherein the detection means detects for non-zero signals, wherein any inhomogeneities or defects present in the material alter the diffusion, either by enhancing recombination or altering diffusion coefficients, of one or both of the photogenerated carrier density waves which no longer interfere destructively and thus produce a non-zero signal, and the processing means calculating therefrom maps of any inhomogeneities or defects that affect carrier density, and wherein the theoretical model includes an effective carrier diffusion model to obtain quantitative values for the selected properties of the material, and wherein the processing means combines quantitative results of the theoretical model with maps produced from spatially scanning across the first and second opposed surfaces of the material to provide quantitative imaging of the material.

49. The apparatus according to claim 48 wherein the selected properties calculated from the theoretical model include carrier recombination lifetime, $\tau$, carrier diffusivity, D, surface recombination velocities, S, carrier diffusion lengths, L, and carrier mobility, $\mu$, and space charge layer width, W.

50. The apparatus according to claim 48 wherein the excitation source is a laser modulated at a modulation frequency, including scanning the modulation frequency in a pre-selected range, and wherein the theoretical model includes an effective carrier diffusion model to calculate the selected properties of the material irradiated with a modulated laser, and combining quantitative results of the theoretical model with the maps produced from spatially scanning across at least one surface of the material to provide quantitative imaging of the material.

51. The apparatus according to claim 48 wherein the excitation source is a laser pulsed for a given time duration, including scanning the time duration of the pulses in a pre-selected range, and wherein the theoretical model includes an effective carrier diffusion model to calculate the selected properties of the material irradiated with a pulsed laser, and combining quantitative results of the theoretical model with maps produced from spatially scanning across at least one surface of the material to provide quantitative imaging of the material.

52. The apparatus according to claim 48 wherein the maps produced from scanning at least one surface of the material is combined with calibration curves to provide quantitative imaging of the material.

53. The apparatus according to claim 42 wherein the excitation source is an optical excitation source pulsed in time domain.

54. The apparatus according to claim 42 wherein the excitation source is an optical excitation source modulated in frequency domain.

55. The apparatus according to claim 42 wherein said excitation source is a laser.

56. The apparatus according to claim 55 wherein said laser is a solid state laser.

57. The apparatus according to claim 56 wherein said solid state laser is modulated by current modulation.

58. The apparatus according to claim 55 wherein the laser is a gas laser.

59. The apparatus according to claim 42 wherein the filtering means for filtering Planck-mediated emissions from the recombination-induced infrared emission includes a filter having a narrow spectral window that attenuates wavelengths in a wavelength band from about 7 to 12 $\mu$m.

60. The apparatus according to claim 42 wherein the detection means is a room temperature solid state detector.

61. The apparatus according to claim 60 wherein the room temperature solid state detector is an InGaAs solid state detector.

62. The apparatus according to claim 42 wherein the detection means is a cooled solid state detector.

63. The apparatus according to claim 42 wherein said detection means is a multi-element array detector to rapidly image a large surface area of the surface of the material.

64. The apparatus according to claim 63 wherein said multi-element array detector produces a signal array processed under parallel lock-in detection by oversampling the array at least four times per period, manipulating by sine and cosine modulation factors the elements of the array, storing them under in-phase and quadrature labels, and combining to construct demodulated lock-in amplitude and phase photocarrier radiometry (PCR) images of the array.

65. The apparatus according to claims 42 wherein said detection means is a single element detector.

66. The apparatus according to claim 42 wherein the excitation source is one of an electron beam source, a flashlamp, a light emitting diode (LED), or any other electromagnetic wave source, which produces a photon beam having sufficient energy to excite carriers in the semiconductor or optical material.

67. The apparatus according to claim 42 wherein the excitation source means is modulated by a mechanical chopper.

68. The apparatus according to claim 42 wherein the excitation source means is modulated by an acousto-optic modulator.

69. The apparatus according to claim 42 wherein the excitation source means is modulated by an electro-optic modulator.

70. The apparatus according to claim 42 wherein the detection means includes a filter for blocking the energy beam from the excitation source from irradiating the detection means.

* * * * *